United States Patent [19]
Scanlan et al.

[11] Patent Number: 6,107,517
[45] Date of Patent: Aug. 22, 2000

[54] THYROID HORMONE ANALOGUES AND METHODS FOR THEIR PREPARATION

[75] Inventors: Thomas S. Scanlan; Hikari A.I. Yoshihara; Grazia Chiellini, all of San Francisco, Calif.; Timothy J. Mitchison, Brookline, Mass.

[73] Assignee: The Regents of the University of California, Oakland, Calif.

[21] Appl. No.: 09/345,673

[22] Filed: Jun. 30, 1999

Related U.S. Application Data

[60] Provisional application No. 60/091,185, Jun. 30, 1998.

[51] Int. Cl.⁷ .................................................. C07C 59/48
[52] U.S. Cl. .......................... 562/471; 514/543; 514/570; 560/9; 560/52; 560/57; 560/61; 562/464; 562/471; 562/426
[58] Field of Search ..................................... 514/543, 570; 560/52, 57, 61, 9; 562/471, 464, 426

[56] References Cited

U.S. PATENT DOCUMENTS

| | | | |
|---|---|---|---|
| 3,332,957 | 7/1967 | Bencze | 546/239 |
| 4,072,705 | 2/1978 | Mieville | 514/543 |
| 4,323,691 | 4/1982 | Ours et al. | 560/36 |
| 5,883,294 | 5/1999 | Scanlan et al. | 562/471 |

OTHER PUBLICATIONS

Apriletti et al., "Expression of the Rat α1 Thyroid Hormone Receptor Ligand Binging Domain in Escherichia coli and the Use of a Ligand–Induced Conformation Change as a Method for Its Purification to Homogeneity," Protein Expression and Purification, vol. 6, pp. 363–370, 1995.

Apriletti et al., "Large Scale Purification of the Nuclear Thyroid Hormone Receptor from Rat Liver and Sequence–Specific Binding of the Receptor to DNA," J. Biol. Chem., vol. 263, No. 19, pp. 9409–9417, 1988.

Chiellini et al., "A High–Affinity Subtype–Selective Agonist Ligand for the Thyroid Hormone Receptor," Chemistry and Biology, vol. 5, No. 6, pp. 299–306, 1998.

Luengo et al., "Manipulation of the Rapamycin Effector Domain. Selective Nucleophilic Substitution of the $C_7$ Methoxy Group," J. Org. Chem., vol. 59, pp. 6512–6513, 1994.

Luengo et al., "Structure–Activity Studies of Rapamycin Analogs: Evidence that the C–7 Methoxy Group Is Part of the Effector Domain and Positioned at the FKBP12–FRP Interface," Chemistry and Biology, vol. 2, pp. 471–481, 1995.

Ribeiro et al., "Mechanisms of Thyroid Hormone Action: Insights from X–ray Crystallographic and Functional Studies," Recent Progress in Hormone Research, vol. 53, 351–394, 1998.

Ribeiro et al., "Thyroid Hormone Export Regulates Cellular Hormone Content and Response," J. Biol. Chem., vol. 271, No. 29, pp. 17147–17151, 1996.

*Primary Examiner*—Paul J. Killos
*Assistant Examiner*—Taylor V. Oh
*Attorney, Agent, or Firm*—Cooley Godward LLP

[57] ABSTRACT

Thyroid hormone analogues are disclosed. Methods of using such analogues and pharmaceutical compositions containing them are also disclosed, as are novel procedures for their preparation.

39 Claims, No Drawings

THYROID HORMONE ANALOGUES AND METHODS FOR THEIR PREPARATION

This application claims benefit of Provisional application 60/091,185 filed Jun. 30, 1998.

This invention was made with Government Support under Grant No. DK52798, awarded by the National Institutes of Health. The Government has certain rights to this invention.

INTRODUCTION

1. Technical Field

This invention relates to thyroid hormone agonists and antagonists, methods of using such compounds, and pharmaceutical compositions containing them. The invention also relates to methods of preparing such compounds.

2. Background

Nuclear receptors represent a superfamily of proteins that specifically bind a physiologically relevant small molecule, such as hormone or vitamin. As a result of a molecule binding to a nuclear receptor, the nuclear receptor changes the ability of a cell to transcribe DNA, i.e. nuclear receptors modulate the transcription of DNA, although they may have transcription independent actions. Unlike integral membrane receptors and membrane associated receptors, the nuclear receptors reside in either the cytoplasm or nucleus of eukaryotic cells. Thus, nuclear receptors comprise a class of intracellular, soluble ligand-regulated transcription factors.

Nuclear receptors include receptors for thyroid hormones. Thyroid hormones promote normal growth and development and control an extraordinary number of regulatory functions in mammals. They regulate fetal development, cholesterol metabolism, the level of obesity, free radical formation, intestinal and cardiovascular functions, and bone and calcium metabolism. In current medical practice, thyroid hormones are used mostly for replacement therapy for humans with hypothyroidism, and to suppress the pituitary gland stimulation of the thyroid gland in patients with thyroid nodules or cancer. However, these hormones cannot be administered in high doses because of significant side effects, mainly on the heart.

There are two major subtypes of the thyroid hormone receptor ("TR"), TRα and TRβ, and they are expressed from two different genes. Preliminary experiments indicate that the α and β subtypes are differentially expressed in various tissues.

It is desirable to produce thyroid hormone agonists and antagonists that are selective for TRα and TRβ. Surprisingly, a small class of halogen-free thyroid hormone agonists has been discovered, which are highly selective for the TRβ subtype with high binding affinity, and are described in U.S. Pat. No. 5,883,294, the complete disclosure of which is hereby incorporated by reference. Another previous disclosure of interest is U.S. patent application 08/764,870, filed Dec. 13, 1995, the complete disclosure of which is hereby incorporated by reference.

Although antagonist ligands have been developed for a number of nuclear receptors, there is currently no reported high-affinity antagonist for the TR. Examination of known nuclear receptor antagonist ligands reveals that these compounds structurally resemble their agonist counterparts but contain a large (>8 carbon atom) extension group attached to the middle of the molecule, Ribeiro, et al., *Recent Prog. Horm. Res.* 53:351–394 (1998).

A high affinity TRβ-selective agonist ligand, designated GC-1, was recently prepared and characterized, Chiellini, et al., *Chemistry & Biology* 5:299–306 (1998). GC-1 contains several structural differences from 3,5,3'-triodo-L-thyronine ("$T_3$"), the major active form of thyroid hormone. In particular, the methylene unit bridging the two phenyl rings introduces a new derivatizable position in the middle of the molecule which is unavailable in the natural ligand where an ether oxygen joins the rings.

It would be highly desirable to design a route for the efficient derivatization of the bridging carbon present on the GC-1 family of compounds with a panel of nucleophiles. This has been successful in the preparation of semi-synthetic rapamycin derivatives by using an $S_N1$ reaction, Luengo, et al., *J. Org. Chem.*, 59:6512 (1994) and Luengo, et al., *Chem. Biol.*, 2:471 (1995). The resulting GC-1 derivatives can then be converted to thyromimetics using the same chemistry that was established for the synthesis of GC-1. It is expected that these thyronilmetics, which contain an extension group attached to the middle of a TR agonist, would be high-affinity antagonists of TR.

SUMMARY OF THE INVENTION

The present invention relates to compounds of Formula I:

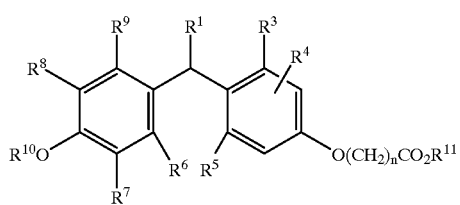

wherein:

n is 1, 2 or 3;

$R^1$ is $C_{1-2}$alkyl, $C_{3-12}$alkanol, $C_{2-6}$alkenyl, $C_{5-12}$alkenol, heterocyclo, aryl substituted with at least one electron-donating group, —$OR^2$ or —$SR^2$, where $R^2$ is $C_{1-12}$alkyl or aryl, or —A—C(O)$NR^{12}R^{13}$, where A is $C_{2-15}$alkyl or $C_{4-15}$alkenyl and $R^{12}$ and $R^{13}$ are $C_{1-6}$alkyl;

$R^3$ and $R^5$ are methyl;

$R^4$ is hydrogen, $C_{1-6}$alkyl or cycloalkyl;

$R^6$ and $R^9$ are hydrogen or $C_{1-6}$alkyl;

$R^7$ and $R^8$ are independently hydrogen, halogen, $C_{1-6}$alkyl, optionally substituted phenyl, optionally substituted benzyl, or heteroaryl; with the proviso that $R^7$ and $R^8$ cannot both be hydrogen;

$R^{10}$ is hydrogen, $C_{1-6}$alkyl, cycloalkyl, or acyl; and $R^{11}$ is hydrogen, $C_{1-6}$alkyl, or cycloalkyl; and the pharmaceutically acceptable salts thereof.

In a second aspect, the invention relates to a method of treatment of mammals having a disease state that is treatable by thyroid hormones, comprising administering a therapeutically effective dose of a compound of Formula I.

In a third aspect, the invention relates to a pharmaceutical composition containing a therapeutically effective amount of a compound of Formula I admixed with at least one pharmaceutically acceptable excipient.

In a fourth aspect, the invention relates to processes for preparing the compounds of Formula I.

The invention also relates to compounds of Formula II:

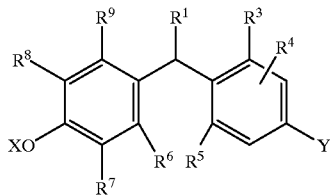

II where Y is —TO or —O(CH$_2$)$_n$CO$_2$C$_{1-6}$alkyl; X and T are protecting groups, and n, R$^1$ and R$^3$–R$^9$ are as defined above.

In another aspect, the invention relates to the use of a compound of Formula II as an intermediate in the process for preparing the compounds of Formula I.

The invention also relates to compounds of Formula III:

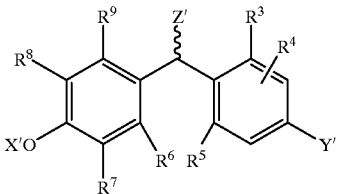

III where Y' is —OT' or —O(CH$_2$)$_n$CO$_2$C$_{1-6}$alkyl; X' and T' are protecting groups, and at least one of said protecting groups is a silyl containing protecting group; Z' is a leaving group and n and R$^3$–R$^9$ are as defined above.

In another aspect, the invention relates to the use of a compound of Formula HII as an intermediate in the process for preparing the compounds of Formula I.

In yet another aspect, the invention pertains to the processes for preparing compounds of Formulas II and III.

DETAILED DESCRIPTION OF THE INVENTION

The invention relates to a family of compounds useful for treating a disease state that is treatable by thyroid hormones. These compounds have the Formulas I, II and III as set forth below.

The present invention relates to compounds of Formula I:

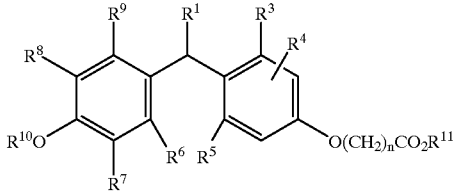

I wherein:

n is 1, 2 or 3;

R' is C$_{1-12}$alkyl, C$_{3-12}$alkanol, C$_{2-6}$alkenyl, C$_{5-12}$alkenol, heterocyclo, aryl substituted with at least one electron-donating group, —OR$^2$ or —SR$^2$, where R$^2$ is C$_{-12}$alayl or aryl, or —A—C(O)NR$^{12}$R$^{13}$, where A is C$_{1-5}$alkyl or C$_{4-15}$alkenyl and R$^{12}$ and R$^{13}$ are C$_{1-6}$alkyl;

R$^3$ and R$^5$ are methyl;

R$^4$ is hydrogen, C$_{1-6}$alkyl or cycloalkyl;

R$^6$ and R$^9$ are hydrogen or C$_{1-6}$alkyl;

R$^7$ and R$^8$ are independently hydrogen, halogen, C$_{1-6}$alkyl, optionally substituted phenyl, optionally substituted benzyl, or heteroaryl; with the proviso that R$^7$ and R$^8$ cannot both be hydrogen;

R$^{10}$ is hydrogen, C$_{1-6}$alkyl, cycloalkyl, or acyl; and

R$^{11}$ is hydrogen, C$_{1-6}$alkyl, or cycloalkyl; and the pharmaceutically acceptable salts thereof.

The invention also relates to compounds of Formula II, which find utility as intermediates in the process for preparing the compounds of Formula I:

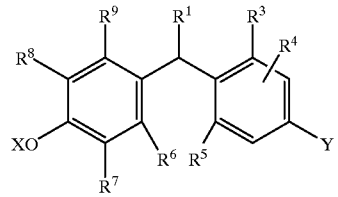

II where Y is —TO or —O(CH$_2$)$_n$CO$_2$C$_{1-6}$alkyl; X and T are protecting groups, and n, R$^1$ and R$^3$–R$^9$ are as defined above.

The invention also relates to compounds of Formula III, which find utility as intermediates in the process for preparing the compounds of Formula I:

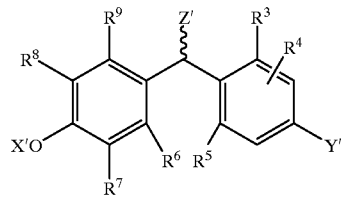

III where Y' is —OT' or —O(CH$_2$)nCO$_2$C$_{1-6}$alkyl; X' and T' are protecting groups, and at least one of said protecting groups is a silyl containing protecting group; Z' is a leaving group and n and R$^3$–R$^9$ are as defined above.

Definitions

As used herein:

"Alkyl" means a branched or unbranched saturated monovalent hydrocarbon radical containing 1 to 20 carbon atoms (C$_{1-20}$alkyl), more typically Cl-$_{12}$alkyl, such as methyl, ethyl, propyl, tert-butyl, n-hexyl, n-octyl and the like. "Lower alkyl" means an alkyl group containing 1 to 6 carbon atoms, such as methyl, ethyl, propyl, isopropyl, tert-butyl, butyl, n-hexyl and the like, unless otherwise indicated.

"Cycloalkyl" as used herein means a saturated monovalent monocyclic hydrocarbon radical containing 3–12 carbon atoms, such as cyclopropyl, cyclobutyl, cyclopentyl, cyclohexyl, cycloheptyl and cyclooctyl. The radical may be optionally mono-, di-, or tri-substituted, independently, with alkyl, lower alkyl, cycloalkyl, hydroxy-lower alkyl, amino-lower alkyl, hydroxyl, thiol, amino, halo, nitro, lower alkylthio, lower alkoxy, mono-lower alkylamino, di-lower alkylamino, hydroxycarbonyl, lower alkoxycarbonyl, hydroxysulfonyl, lower alkoxysulfonyl, lower alkylsulfonyl, lower alkylsulfinyl, trifluoromethyl, cyano, tetrazoyl, carbamoyl, lower alkylcarbarnoyl, and di-lower alkylcarbamoyl.

"Lower alkoxy" or "C$_{1-6}$alkoxy" means the group —O— (lower alkyl), wherein lower alkyl is as herein defined.

"Alkenyl" means an unsaturated branched or straight chain or alkene radical containing 2 to 12 carbon atoms and containing a double bond. "Lower alkenyl" or "$C_{2-6}$alkenyl" refers to an alkenyl radical of 2–6 carbon atoms and containing a double bond. The term is further exemplified by such radicals as ethylene and propylene.

"Alkanol" and "alkenol" are terms used to mean an alkyl or alkenyl group that is substituted with a hydroxyl group. Accordingly, "$C_{3-12}$alkanol" is an alkyl group having 3–12 carbons and an —OH group, while "$C_{5-12}$alkenol" is an alkenyl group having 5–12 carbons and an —OH group.

"Halo" or "halogen" means fluoro, chloro, bromo, or iodo.

The term "aryl" refers to a monovalent unsaturated aromatic carbocyclic radical having a single ring (e.g., phenyl) or two rings (e.g., naphthyl or biphenyl), which can optionally be mono-, di- or tri-substituted, independently, with OH, COOH, lower alkyl, lower alkoxy, nitro, amino, alkylamino, dialkylamino, trifluoromethyl and/or cyano.

The term "acyl" refers to the group —C(O)R, where R is lower alkyl or cycloalkyl, for example acetyl, propionyl, cyclopropionyl, butanoyl, and the like.

The term "heteroatom" refers to oxygen, sulfur and nitrogen, unless otherwise specified.

The term "heterocycloalkyl" refers to a cycloalkyl radical, as defined above, having 1–3 heteroatoms within the ring (e.g., piperidinyl, piperazinyl, pyrrolidinyl, pyrrolodinonyl, tetrahydrofuranyl, morpholinyl, tetrahydrothiophenyl, and the like). The term "heteroaryl" refers to an aryl radical, as defined above, having 1–3 heteroatoms within a single ring (e.g., pyridyl, imidazolyl, thiazolyl, pyrimidine, oxazolyl, and the like). The term "heterocyclo" is used to collectively refer to heterocycloalkyl and heteroaryl radicals. The heterocyclo radical can optionally be mono-, di- or tri-substituted, independently, with OH, COOH, lower alkyl, lower alkoxy, nitro, amino, alkylamino, dialkylamino, trifluoromethyl and/or cyano. The term "heterocyclo" also includes instances where an atom of the heterocyclo has been oxidized, e.g., N-oxides, sulfoxides and sulfones.

The term "electron-donating group" refers to a substituent which, when bound to a molecule, is capable of polarizing the molecule such that the electron-donating group becomes electron poor and positively charged relative to another portion of the molecule, i.e., it has reduced electron density. Such groups include, by way of illustration and not limitation, alkoxys such as methoxy, hydroxy, amines, ethers, thioethers, phosphines, oxyanions, mercaptans, and their anions, sulfides, etc. Similarly, the term "aryl substituted with at least one electron-donating group" refers to an aryl group, preferably phenyl, substituted with at least one, and preferably two, groups that are electron-donating groups.

The term "protecting group" as used herein means a radical group that is covalently bonded to a potentially reactive functionality, masking its reactive nature and thereby preventing undesired side reactions during the course of chemical synthesis. For example, a trialkyl silyl protecting group can serve to protect a hydroxyl functionality, etc. A protecting group preferably is easily attached to the molecule and also has the property that it may be removed selectively at a desired point in the chemical synthesis, under conditions that do not harm other functional groups in the molecule, to yield the unmasked chemical functionality. Suitable protecting groups include lower alkyls such as methyl, and silyl containing protecting groups such as triisopropylsilyl ("TIPS") and tert-butylmethoxyphenylsilyloxy ("TBMPS").

The term "leaving group" as used herein means a group of charged or uncharged atoms that departs during a substitution or displacement reaction. Suitable leaving groups include hydroxy and lower alkoxys.

"Optional" or "optionally" means that the subsequently described event or circumstance may or may not occur, and that the description includes instances where said event or circumstance occurs and instances in which it does not. For example, optionally substituted phenyl indicates either unsubstituted phenyl, or phenyl mono-, di- or tri-substituted, independently, with OH, COOH, lower alkyl, lower alkoxy, halo, nitro, amino, alkylamino, dialkylamino, trifluoromethyl and/or cyano.

As used herein, the terms "inert organic solvent" or "inert solvent" mean a solvent inert under the conditions of the reaction being described in conjunction therewith. Such solvents include, by way of example and not limitation, benzene, toluene, acetonitrile, tetrahydrofuran ("TBF"), N,N-dimethylformamide ("DMF"), chloroform ("$CHCl_3$"), methylene chloride (or dichloromethane or "$CH_2Cl_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable salt" means those salts which retain the biological effectiveness and properties of the compounds of Formula I, and which are not biologically or otherwise undesirable. Such salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

The term "q.s" is used herein to mean adding a quantity sufficient to achieve a stated function., for example to bring a solution to a desired volume (q.s. to 100 ml) or to a desired pH (q.s. to pH 4).

It should be understood that Formula I as drawn is intended to represent the racemic form of compounds of Formula I as well as the individual enantiomers and non-racemic mixtures thereof, although for the sake of clarity only one enantiomer is shown. The scope of the invention as described and claimed encompasses the racemic forms of the compounds of Formula I as well as the individual enantiomers and non-racemic mixtures thereof.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease.

The term "disease state which is alleviated by treatment with a thyroid hormone antagonist" as used herein is intended to cover all disease states which are generally acknowledged in the art to be usefully treated with thyroid hormone antagonists in general, and those disease states which have been found to be usefully treated by the thyroid hormone antagonists of our invention, the compounds of Formula I. Such disease states include, but are not limited to, hyperthyroidism, tachycardia, cardiac arrhythmia, Graves disease, and so forth.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

METHODS OF TREATMENT

The compounds of Formula I can be useful in medical treatments and their biological activity can be measured in the following tests:

(i) the induction of mitochondrial α-glycerophosphate dehydrogenase (GPDH:EC 1.1.99.5). This assay is particularly useful since in certain species e.g. rats it is induced specifically by thyroid hormones and thyromimetics in a close-related manner in responsive tissues e.g. liver, kidney and the heart (Westerfield, W. W., Richert, D. A. and Ruegamer, W. R., Endocrinology, 1965, 77, 802). The assay allows direct measurement in rates of a thyroid hormone-like effect of compounds and in particular allows measurement of the direct thyroid hormone-like effect on the heart;

(ii) the elevation of basal metabolic rate as measured by the increase in whole body oxygen consumption;

(iii) the stimulation of the rate of beating of atria isolated from animals previously dosed with thyromimetics;

(iv) the change in total plasma cholesterol levels as determined using a cholesterol oxidase kit (for example, the Merck CHOD iodine colourimetric kit);

(v) the measurement of LDL (low density lipoprotein) and HDL (high density lipoprotein) cholesterol in lipoprotein fractions separated by ultracentrifugation; and p (vi) the change in total plasma triglyceride levels as determined using enzymatic color tests, for example the Merck System GPO-PAP method.

The compounds of Formula I can be found to exhibit anti-thyromimetic activity in these tests, by: (a) binding to thyroid hormone receptors (α,β) by standard in vitro binding assays, such as are well known in the art; (b) influencing the expression of genes regulated by the thyroid receptor, measure by in vivo or in vitro experiments, such as are well known in the art.

The compounds of Formula I may therefore be used in therapy, in the treatment of conditions which can be alleviated by compounds which antagonize the effects of thyroid hormones in certain tissues. For example, compounds of Formula I which block the effects of the thyroid hormone are indicated in the treatment of hypothyroidism. Such compounds are also indicated for use as anti-arrhythmic agents.

In therapeutic use the compounds of the present invention are usually administered in a standard pharmaceutical composition.

The present invention therefore provides in a further aspect pharmaceutical compositions comprising a compound of Formula I or a pharmaceutically acceptable salt thereof and a pharmaceutically acceptable carrier. Such compositions include those suitable for oral, parenteral or rectal administration.

PHARMACEUTICAL COMPOSITIONS

Compounds of Formula I and their pharmaceutically acceptable salts which are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Compound of Formula I and their pharmaceutically acceptable salts which are active when given parenterally can be formulated for intramuscular or intravenous administration.

A typical composition for intra-muscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

Compounds of Formula I and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula I and their pharmaceutically acceptable salts which are active on topical administration can be formulated as transdermal compositions. Such compositions include, for example, a backing, active compound reservoir, a control membrane, liner and contact adhesive.

The typical daily dose of a compound of Formula I varies according to individual needs, the condition to be treated and with the route of administration. Suitable doses are in the general range of from 0.001 to 10 mg/kg bodyweight of the recipient per day.

Within this general dosage range, doses can be chosen at which the compounds of Formula I lower plasma cholesterol levels and raise metabolic rate with little or no direct effect on the heart. In general, but not exclusively, such doses will be in the range of from 0.5 to 10 mg/kg.

In addition, within the general dose range, doses can be chosen at which the compounds of Formula I lower plasma cholesterol levels and have little or no effect on the heart without raising metabolic rate. In general, but not exclusively, such doses will be in the range of from 0.001 to 0.5 mg/kg.

It is to be understood that the 2 sub ranges noted above are not mutually exclusive and that the particular activity encountered at a particular dose will depend on the nature of the compound of Formula I used.

Preferably, the compound of Formula I is in unit dosage form, for example, a tablet or a capsule so that the patient may self-administer a single dose. In general, unit doses contain in the range of from 0.05–100 mg of a compound of Formula I. Preferred unit doses contain from 0.05 to 10 mg of a compound of Formula I.

The active ingredient may be administered from 1 to 6 times a day. Thus daily doses are in general in the range of from 0.05 to 600 mg per day. Preferably, daily doses are in the range of from 0.05 to 100 mg per day. Most preferably from 0.05 to 5 mg per day.

As mentioned above, the present invention relates to compounds of Formula I:

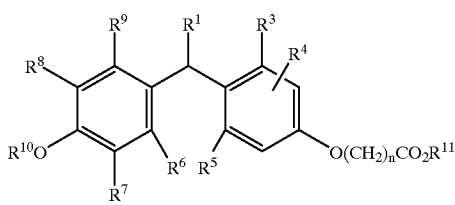

(I)

where n is 1, 2 or 3; $R^1$ is $C_{1-2}$alkyl, $C_{3-12}$alkanol, $C_{2-6}$alkenyl, $C_{5-12}$alkenol, heterocyclo, aryl substituted with at least one electron-donating group, —OR or —SR$^2$, where $R^2$ is $C_{1-12}$alkyl or aryl, or —A—C(O)NR$^{12}$R$^{13}$, where A is $C_{2-15}$alkyl or $C_{4-15}$alkenyl and $R^{12}$ and $R^{13}$ are $C_{1-6}$alkyl; $R^3$ and $R^5$ are methyl; $R^4$ is hydrogen, $C_{1-6}$alkyl or cycloalkyl; $R^6$ and $R^9$ are hydrogen or $C_{1-6}$alkyl; $R^7$ and $R^8$ are independently hydrogen, halogen, $C_{1-6}$alkyl, optionally substituted phenyl, optionally substituted benzyl, or heteroaryl; with the proviso that $R^7$ and $R^8$ cannot both be hydrogen; $R^{10}$ is hydrogen, $C_{1-6}$alkyl, cycloalkyl, or acyl; and $R^{11}$ is hydrogen, $C_{1-6}$alkyl, or cycloalkyl.

In preferred embodiments, n is 1. Preferred $R^4$, $R^6R^7,R^9$, $R^{10}$ and $R^{11}$ substituents are hydrogen. $R^8$ is preferably $C_{1-6}$alkyl, for example, isopropyl.

The R' substituent is preferably $C_{2-6}$alkenyl; phenyl substituted with at least one, preferably two, electron-donating groups; —OR$^2$ or —SR$^2$, where $R^2$ is $C_{1-6}$alkyl or phenyl; $C_{3-12}$alkanol; or —A—C(O)NR$^{12}$R$^{13}$, where A is $C_{2-15}$alkyl or $C_{4-15}$alkenyl and $R^{12}$ and $R^{13}$ are $C_{1-6}$alkyl. A preferred —OR$^2$ substituent is ethoxy. Preferred —SR$^2$ substituents include ethylthio and phenylthio.

Another preferred R' substituent is $C_{2-6}$alkenyl, for example —CH$_2$—CH=CH$_2$. A preferred $R^1$ substituent is also a phenyl substituted with at least one, preferably two, electron-donating groups such as methoxy, for example, dimethoxyphenyl. A preferred $C_{3-2}$alkanol is —(CH$_2$)$_3$—OH. Preferred —A—C(O)NR$^{12}$R$^{13}$ groups include —(CH$_2$)$_{10}$—C(O)—N(CH$_3$)—(CH$_2$)$_3$(CH$_3$) and —(CH$_2$)$_2$—C=C—(CH$_2$)$_6$—C(O)—N(CH$_3$)—(CH$_2$)$_3$(CH$_3$).

METHODS OF PREPARATION

Compounds of Formula I are prepared from an intermediate of Formula II or Formula IIa, which is formed from the intermediates (3) and (6), the preparation of which is shown below.

Suitable protecting groups for the X substituent of Formula II include, but are not limited to, silyl containing protecting groups such as TIPS. Suitable protecting groups for the Y substituent of Formula II include, but are not limited to, —OT where T is $C_{1-6}$alkyl such as methyl, and —O(CH$_2$)$_n$CO$_2$Me and —O(CH$_2$)nCO$_2$Et.

1. Preparation of Compounds of Formula II
1a. Preparation of Compounds of Formula (3)
Compounds of Formula (3) are prepared as shown below in Reaction Scheme I.

Reaction Scheme I

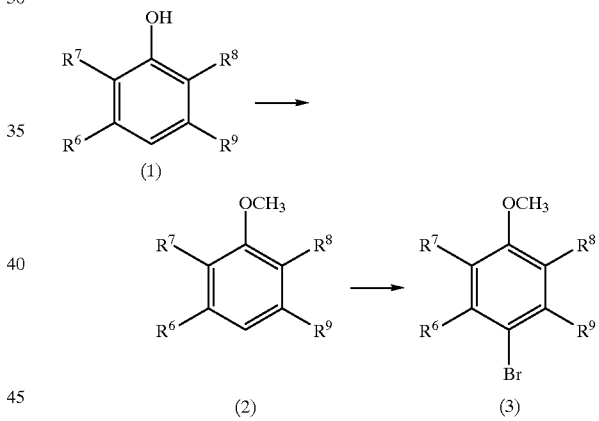

Compounds of Formula (1) are commercially available, or may be prepared by means well known in the art. In general, the phenol of Formula (1) is first protected by conversion to It the methoxy derivative, for example by reacting (1) with methyl iodide in the presence of a base, for example potassium carbonate, in a polar solvent, for example DMF. When the reaction is substantially complete, the protected phenol of Formula (2) is isolated and purified by conventional means, preferably by flash chromatography.

Clearly, other conventional phenol protecting groups could be utilized instead of methoxy, for example a silyl protecting group, e.g. t-butyldimethylsilyloxy.

The compound of Formula (2) is then brominated using potassium bromide in the presence of a crown ether, for example 18-crown-6, and an oxidizing agent, for example 3-chloroperoxy benzoic acid. The reaction is carried out in an inert solvent, preferably CH$_2$Cl$_2$. When the reaction is substantially complete, the 4-bromo derivative of Formula (3) is isolated and purified by conventional means, preferably by flash chromatography.

1b. Preparation of Compounds of Formula (6)

Compounds of Formula (6) are prepared as shown below in Reaction Scheme II.

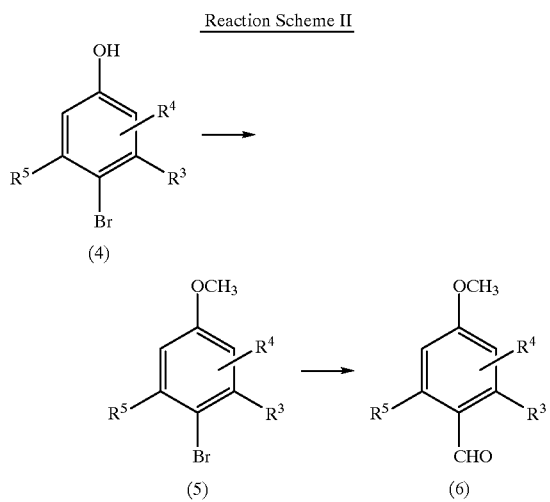

Compounds of Formula (4) are commercially available, or may be prepared by means well known in the art. In general, the phenol of Formula (4) is first protected by conversion to the methoxy derivative, or other conventional phenol protecting groups, as disclosed in Reaction Scheme I above, to give a p-bromo compound of Formula (5).

The bromo moiety of the compound of Formula (5) is then converted to a formyl group. The reaction is carried out conventionally, adding t-butyllithium to a solution of (5) in an inert lid solvent at about −78° C., preferably THF, and adding DMF to the cold solution. After stirring cold, the mixture is allowed to warm to room temperature. When the reaction is substantially complete, the 4-formyl derivative of Formula (6) is isolated and purified by conventional means, preferably by flash chromatography.

1c. Preparation of Compounds of Formula II from Compounds of Formulas (3) and (6)

Compounds of Formula II are prepared from (3) and (6) as shown below in Reaction Scheme III.

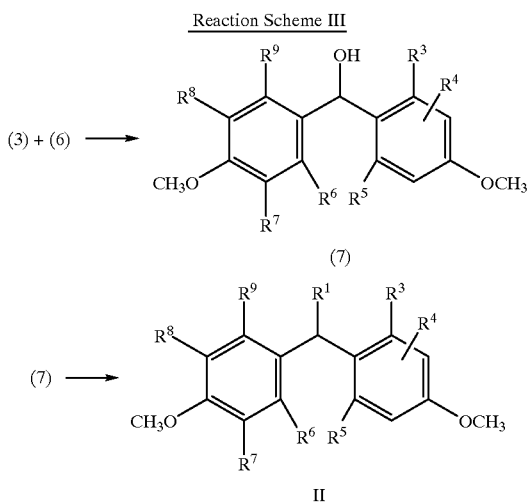

Compounds of Formula (7) are prepared by reaction of (3) and (6). In general, the p-bromo compound of Formula (3) is dissolved in an inert solvent, preferably THF, cooled to about −78° C., and t-butyllithium added. After stirring for about 10 minutes, the compound of Formula (6) is added. After stirring cold, the mixture is allowed to warm to room temperature. When the reaction is substantially complete, the carbinol derivative of Formula (7) is isolated and purified by conventional means, preferably by flash chromatography.

Solvolysis of the benzylhydroxy group of the compound of Formula (7) yields the compound of Formula II. In general, the reaction is carried out with $CH_2Cl_2$ in an acidic 1(Q medium, preferably trifluoroacetic acetic acid ("TFA"), under an inert atmosphere at about—45° C. in the presence of a suitable acid-stable nucleophilic species, as described in Luengo, et al., *J. Org. Chem.* 59:6512 (1994) and Luengo, et al., *Chem. Biol.* 2:471 (1995). Particularly suitable nucleophiles include ethanol, allyltrimethylsilane, 1,3-dimethoxybenzene, ethanethiol and thiophenol. When the reaction is substantially complete, the compound of Formula II is isolated by conventional means, and preferably used with no further purification.

2. Preparation of Compounds of Formula I from Compounds of Formula II

Compounds of Formula I are prepared from II as shown below in Reaction Scheme IV.

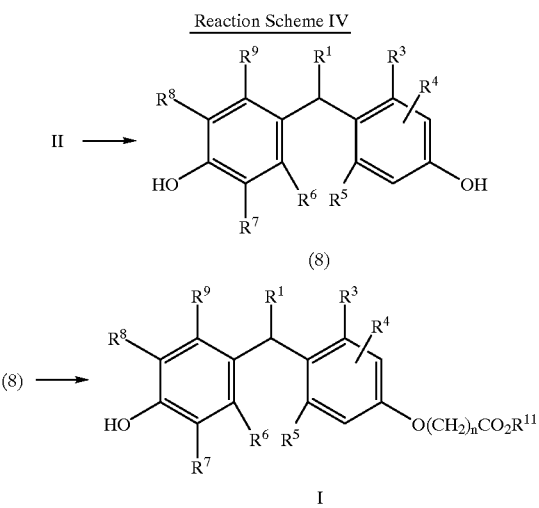

The dimethoxy derivative of Formula II is demethylated. The reaction is carried out conventionally, using boron tribromide in $CH_2Cl_2$. When the reaction is substantially complete, the dihydroxy derivative of Formula (8) is isolated and purified by conventional means, preferably by flash chromatography.

The compound of Formula (8) is then converted to a compound of Formula I where $R^{10}$ is hydrogen by reaction with an ester of formula $Q$-$(CH_2)_n$—$CO_2R^{11}$, where Q is chloro, bromo or iodo, n is 1, 2 or 3, and $R^{11}$ is lower alkyl, for example t-butyl. The compound of Formula (8) is lo; dissolved in an inert solvent, for example THF, cooled to about −25° C., and cesium carbonate ($Cs_2CO_3$) added followed by the halo ester. The mixture is stirred cold for about 1 hour, then allowed to warm to room temperature. When the reaction is substantially complete, the ester derivative of a compound of Formula I is isolated and purified by conventional means, preferably by flash chromatography. This ester is dissolved in a protic solvent, preferably methanol, and hydrolysed with a base, preferably sodium hydroxide. After acidification, the compound of Formula I is isolated and purified by conventional means.

In addition, compounds of Formula I can also be prepared from an intermediate of Formula III, which is formed from intermediates of Formula (10) and (13), the preparation of which is shown below.

3. Preparation of Compounds of Formula III

Suitable protecting groups for the X substituent of Formula III include, but are not limited to, silyl containing protecting groups such as TIPS. Suitable protecting groups for the Y substituent of Formula III include, but are not limited to, —O(CH$_2$)$_n$CO$_2$Me, —O(CH$_2$)$_n$CO$_2$Et and —OT' where T' is a silyl containing protecting group such as TBMPS. Suitable Z' groups in Formula III include, but are not limited to hydroxy and lower alkoxy, for example, methoxy and ethoxy.

This synthesis-includes introduction of the TIPS and TBMPS protecting groups to the phenolic hydroxyls. For purposes of illustration, the following reaction schemes illustrate the synthesis of a compound of Formula I where n is 1, $R^8$ is isopropyl and $R^{10}$ and $R^{11}$ are hydrogen. It is understood that by replacing the starting materials with other compounds of Formulas (10) and (13), and following the procedures described below, other compounds of Formula I are prepared.

3a. Preparation of Compounds of Formula (10)

Compounds of Formula (10) are prepared as shown below in Reaction Scheme V.

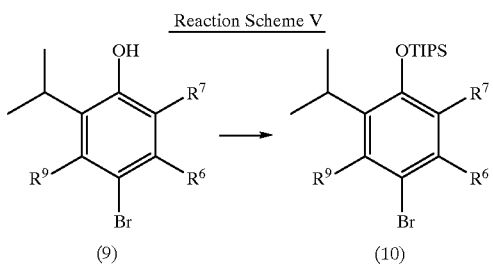

Compounds of Formula (9) are readily synthesized by the addition of 1 equivalent bromine in CH$_2$Cl$_2$ to the commercially available 2-isopropyl phenol. In general, the phenol of Formula (9) is first protected by conversion to the triisopropylsilyloxy derivative with TIPS chloride and imidazole and ClCH$_2$CH$_2$Cl, to give a p-bromo compound of Formula (10). When the reaction is substantially complete, the p-bromo compound is isolated and purified by conventional means, preferably by flash chromatography.

3b. Preparation of Compounds of Formula (13)

Compounds of Formula (13) are prepared as shown below in Reaction Scheme VI.

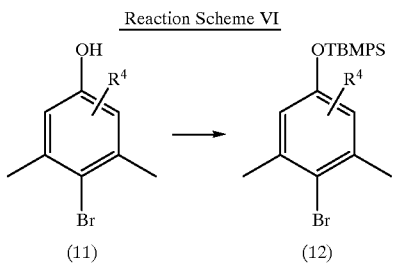

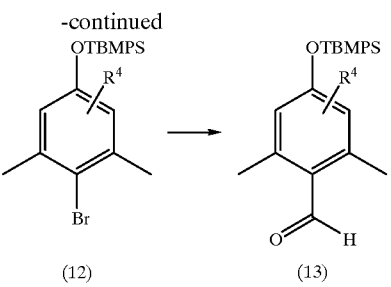

Compounds of Formula (11) are commercially available, or may be prepared by means well known in the art. In general, the phenol of Formula (11) is first protected by conversion to the tert-butylmethoxyphenylsilyloxy derivative with TBMPS bromide in imidazole and CH$_2$Cl$_2$, to give a p-bromo compound of Formula (12).

The bromo moiety of the compound of Formula (12) is then converted to a formyl group. The reaction is carried out conventionally, adding n-butyllithium to a cold solution of (12) in an inert solvent (about −78° C.), preferably THF, and adding DMF to the cold solution. After stirring cold, the mixture is allowed to warm to room temperature. When the reaction is substantially complete, H$_3$O$^+$ is added. The 4-formyl derivative of Formula (13) is then isolated and purified by conventional means, preferably by flash chromatography.

3c. Preparation of Compounds of Formula III from Compounds of Formulas (10) and (13)

Compounds of Formula III are prepared from (10) and (13) as shown below in reaction Scheme VII.

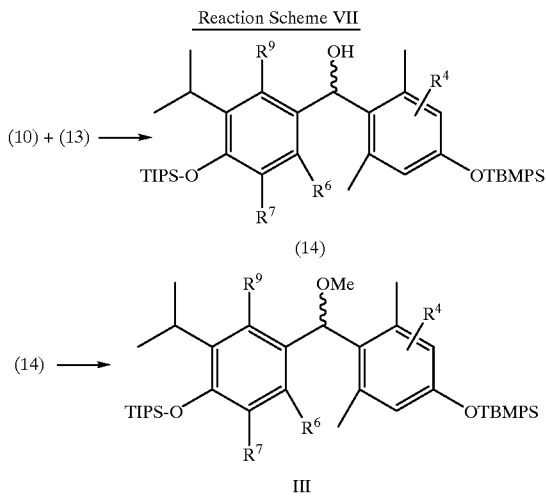

In general, the p-bromo compound of Formula (10) and 1 eq. n-butyllithium are mixed together in a cold inert solvent (e.g., THF at about −78° C.). After stirring for about 10 minutes, this mixture is then added to a suspension of CeCl$_3$, in a cold inert solvent (e.g., THF at about −78° C.) and stirred for about 30 minutes. Then the compound of Formula (13) is added. The reaction is allowed to continue in cold THF (about −78° C.). After stirring cold, the mixture is allowed to warm to room temperature. When the reaction is substantially complete, H$_3$O$^+$ is added. The compound of Formula (14) is isolated and purified by conventional means, preferably by flash chromatography.

Solvolysis of the benzylhydroxy group of the compound of Formula (14) yields the compound of Formula III. In general, the reaction is carried out with CH$_2$Cl$_2$ in an acidic medium, preferably TFA, under an inert atmosphere at about −45° C. in the presence of a suitable acid-stable nucleophilic species, as described in Luengo, et al., *J. Ore. Chem.* 59:6512 (1994) and Luengo, et al., *Chem. Biol.* 2:471 (1995). Particularly suitable nucleophiles include ethanol, methanol, allyltrimethylsilane, 1,3-dimethoxybenzene, ethanethiol and thiophenol. When the reaction is substantially complete, the compound of Formula III is isolated and purified by conventional means, preferably by flash chromatography.

4. Preparation of Compounds of Formula I from Compounds of Formula III

Compounds of Formula I are prepared as shown below in Reaction Scheme VIII.

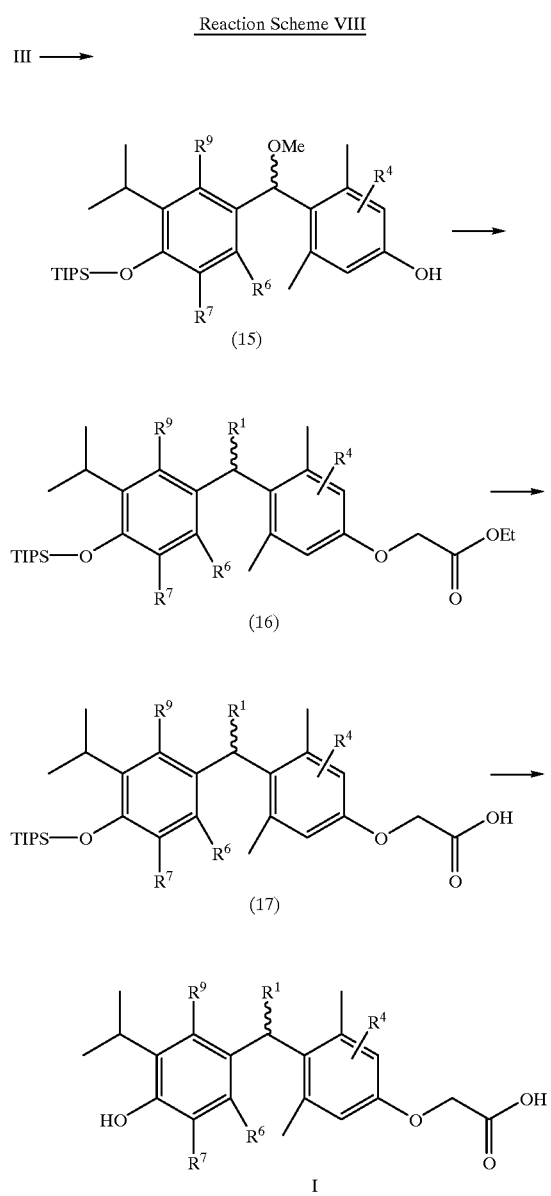

The TBMPS group is removed from the compound of Formula III under conditions that do not harm the sensitive heteroatomic bridge substituents. TBMPS is selectively cleaved with stoichiometric Et$_3$N●3HF in the presence of an inert solvent such as THF (to yield Z'=—OMe as shown in Scheme VII) or stoichiometric tetrabutylammonium fluoride (1 eq. TBAF) in CH$_2$Cl$_2$ to yield Z'=—OEt), at about −78° C. The mixture is washed with a saturated ammonium chloride solution and the aqueous phase extracted with Et$_2$O to yield the phenol of Formula (15).

The resulting phenol is alkylated with an ester of formula Q—(CH$_2$)$_n$—CO$_2$R$^{11}$, where Q is chloro, bromo or iodo, n is 1, 2 or 3, and R$^{11}$ is lower alkyl, for example ethylbromoacetate or methylbromoacetate. Cesium carbonate and the halo ester are added to the phenol in a DMF solution. The mixture is stirred cold for about 1 hour then mixed with a saturated ammonium chloride solution and extracted with Et$_2$O to yield the ester of Formula III (Compound 16), which is then isolated by conventional means.

The next reaction is carried out with CH$_2$Cl$_2$ in an acidic medium, preferably TFA at about −45° C., by the addition of a compound of formula R$^1$—H to the compound of Formula (15). R$^1$ is a lower alkenyl group, an optionally substituted phenyl group, an —OR$^2$ or a —SR$^2$ group, where R$^2$ is lower alkyl or phenyl. If the final product has R$^1$=—OCH$_2$CH$_3$, then this step is optional since the desired R$^1$ substitution may be made during the synthesis of the compound of Formula III.

The ester of Formula (16) is then dissolved in a protic solvent, preferably methanol, and hydrolysed with a base, preferably lithium hydroxide. The mixture is washed with a saturated ammonium chloride solution and the aqueous phase extracted with Et$_2$O to yield the phenol of Formula (17). Subsequent deprotection of the phenol is achieved by dissolving the phenol in equal parts of acetonitrile and CH$_2$Cl$_2$, followed by the addition of 1 eq. potassium fluoride in 0.5 eq. 18-crown-6, to yield the compound of Formula I, which is isolated and purified by conventional means such as reverse phase HPLC.

5. Preparation of Compounds of Formula I, where R$^1$ is A—C(O)NR$^{12}$R$^{13}$ and A is alkyl (I-1)

Compound (I-1) and similar compounds are prepared as shown below in Reaction Scheme IX.

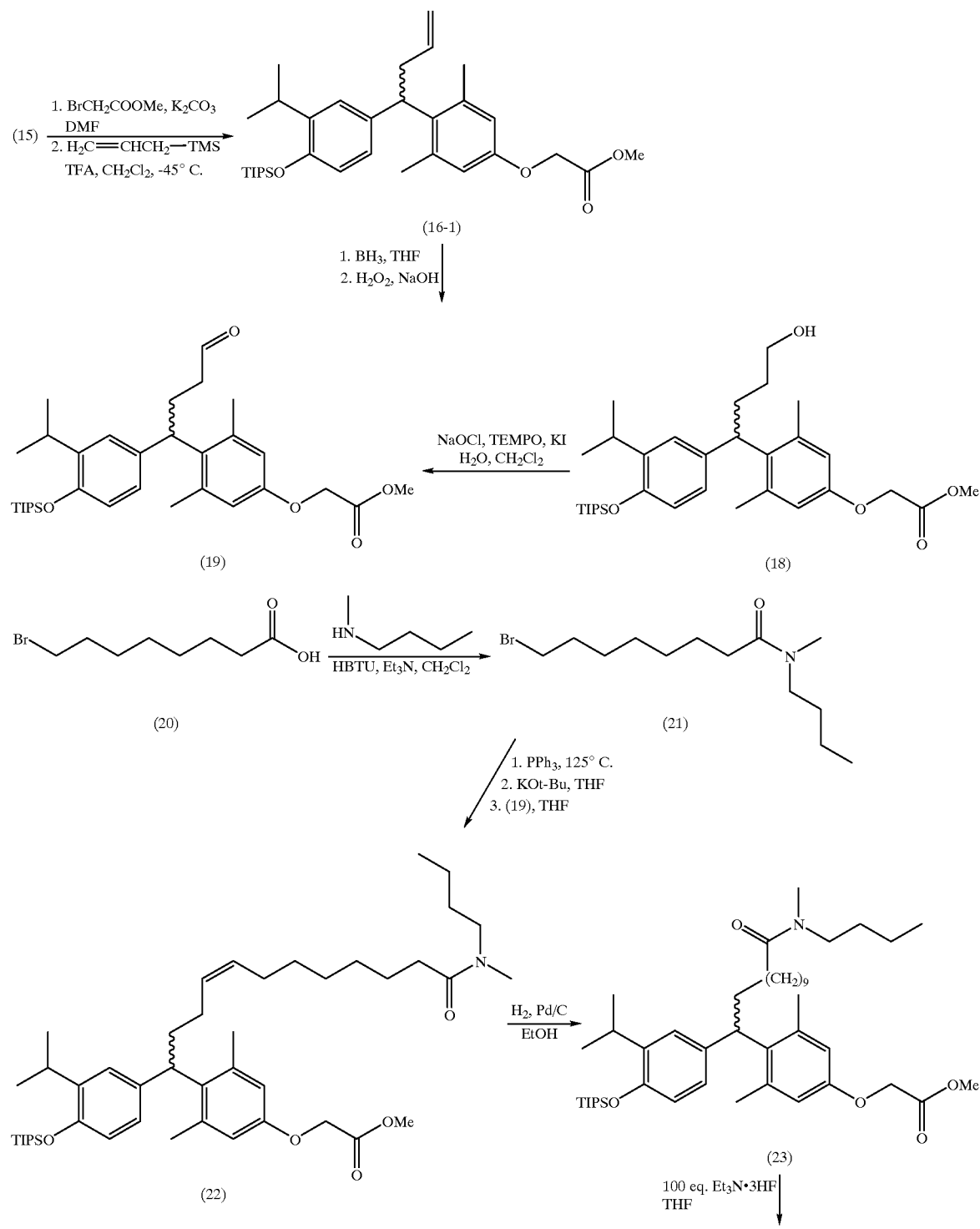
Reaction Scheme IX

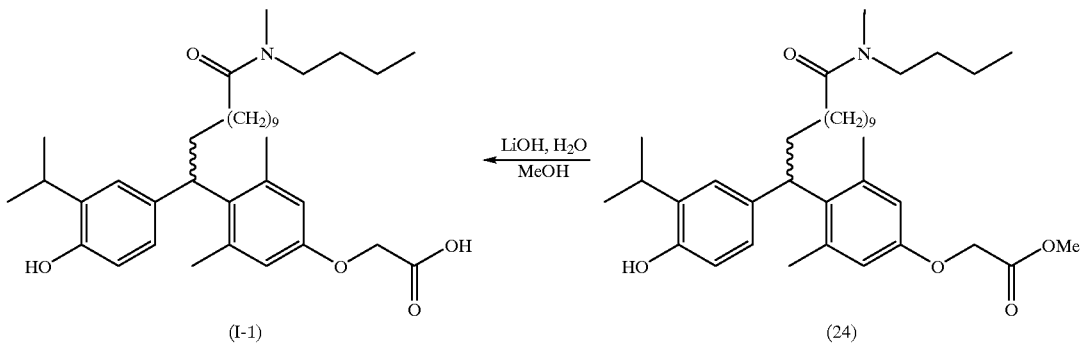
6. Preparation of Compounds of Formula I, where $R^1$ is —A—C(O)NR$^{12}$R$^{13}$ and A is alkenyl (I-2)
Compound (I-2) and similar compounds are prepared as shown below in Reaction Scheme X
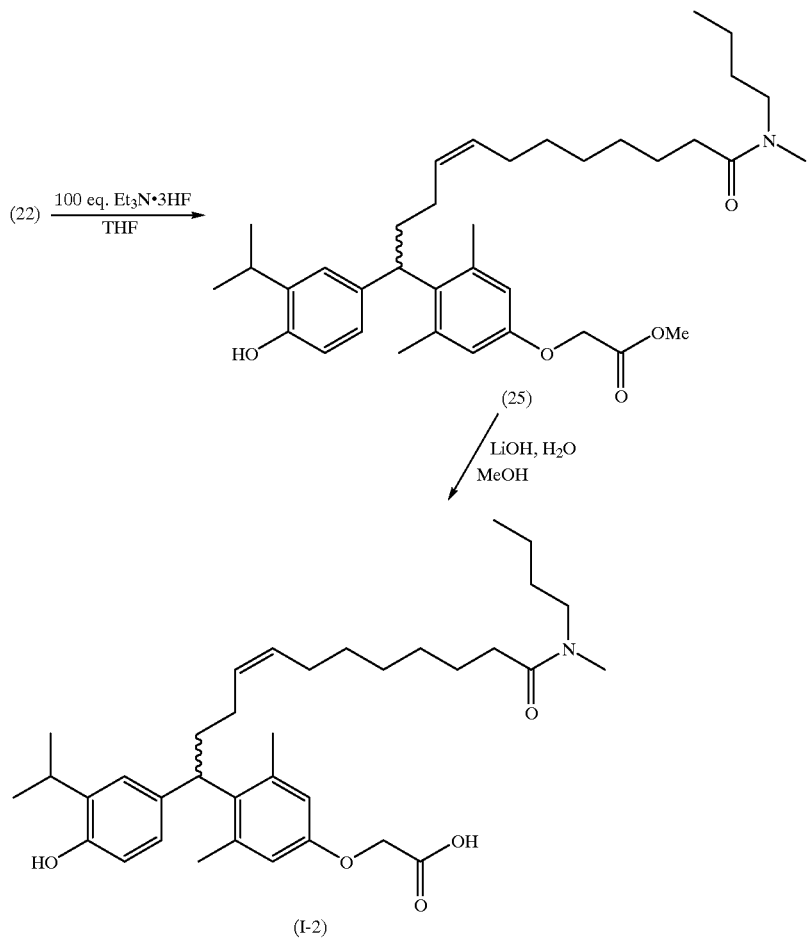

7. Preparation of Compounds of Formula I, where $R^1$ is a lower alkenyl (I-3)
Compound (I-3) and similar compounds are prepared as shown below in Reaction Scheme XI
Reaction Scheme XI
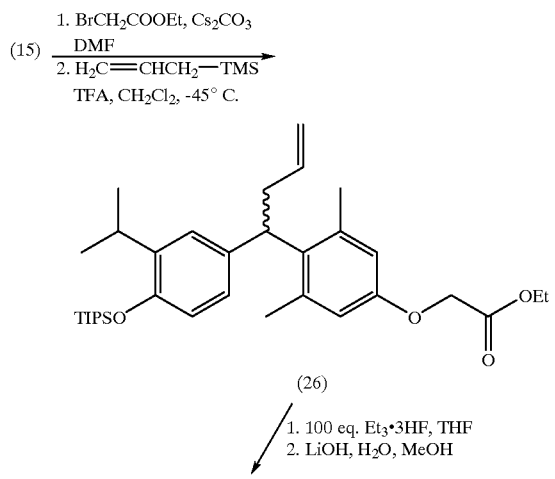
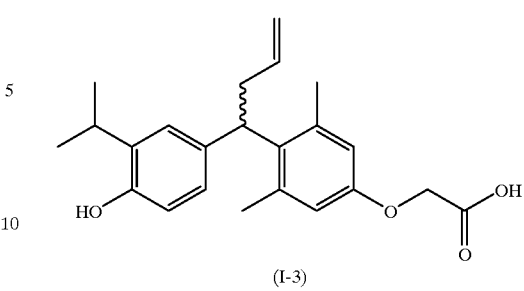
8. Preparation of Compounds of Formula I, where $R^1$ is a lower alkoxy (I-4)
Compound (I-4) and similar compounds are prepared as shown below in Reaction Scheme XII
Reaction Scheme XII
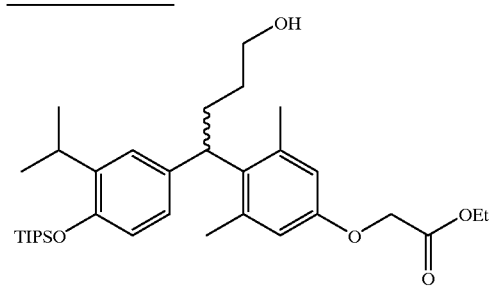
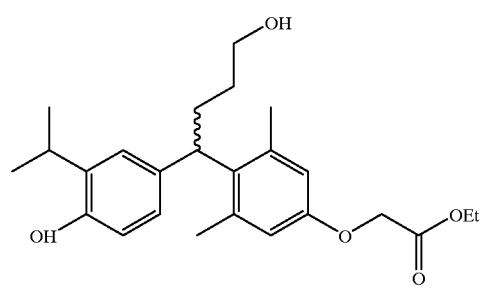

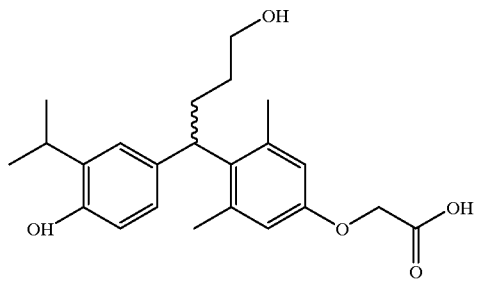
(I-4)
9. Preparation of Compounds of Formula I, where $R^1$ is a substituted aryl (I-5)
Compound (I-5) and similar compounds are prepared as shown below in Reaction Scheme XIII.
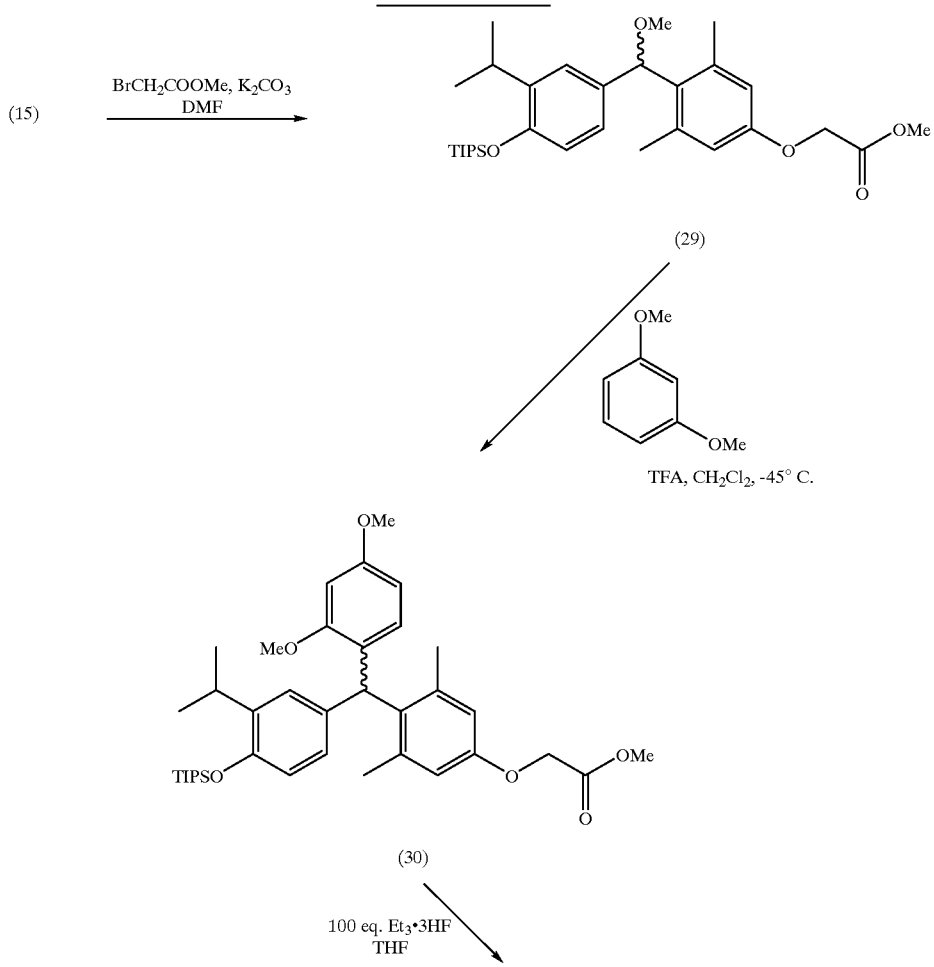

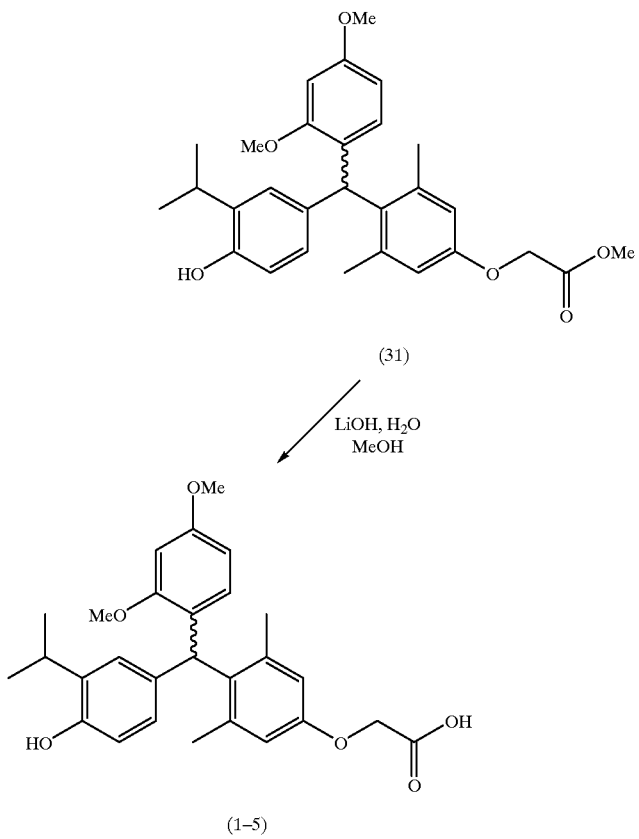

(1-5)

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Separation of Enantiomers

The enantiomers of the compounds and intermediates described herein can be effected, if desired, by any conventional resolution means, for example by separation (e.g. fractional crystallization) of the diastereomeric salts formed by the reaction of a racemic compound of Formula I with an optically active base.

Salts of Compounds of Formula I

The compounds of Formula I where $R^{11}$ is hydrogen may be converted to a corresponding base addition salt from inorganic and organic bases by conventional means. Typically, the free acid of Formula I is dissolved in an inert organic solvent such as diethyl ether, ethyl acetate, chloroform, ethanol or methanol and the like, and the base added in a similar solvent. The temperature is maintained at 0°–50° C. The resulting salt precipitates spontaneously or may be brought out of solution with a less polar solvent.

The following preparation and examples illustrate the invention but are not intended to limit its scope.

General Methods

Proton and carbon-13 nuclear magnetic resonance spectra ($^1$H NMR, $^{13}$C NMR) were obtained on a General Electric QE-300 (300 Mhz) spectrometer, with tetramethylsilane used as the reference.

Flash chromatography on crude products was performed using 230–400 mesh silica gel (Aldrich Chemical Co.). Purity of compounds was determined by TLC using commercial silica gel plates (Alltech, Alugram® Sil G/UV 254) and by $^1$H NMR and HRMS.

Methylene chloride (anhydrous) ($CH_2Cl_2$), THF (anhydrous) and reagents were purchased from Aldrich Chemical Co. and used without further purification. Unless specified otherwise, reactions were performed under Argon inert atmosphere.

| Abbreviations | |
|---|---|
| DMF | N,N-dimethylformamide |
| HBTU | O-(1H-benzotriazol-1-yl)-1,1,3,3-tetramethyl-uronium hexafluorophosphate |
| TBAF | tetrabutylammonium fluoride |
| TBMPS | tert-butylmethoxyphenylsilyloxy |
| TEMPO | 2,2,6,6-tetramethylpiperidine-N-oxide radical |
| TFA | trifluoroacetic acetic acid |
| THF | tetrahydrofuran |
| TIPS | triisopropylsilyl |

EXAMPLE 1

Preparation of Compounds of Formula (2)
Preparation of (2) where $R^7$ is Isopropyl: and $R^6$, $R^8$, $R^9$ are H A mixture of 2-isopropylphenol (a compound of Formula 1) (12.0 g, 88.1 mmol), methyl iodide (25.0 g, 176.2 mmol), and potassium carbonate (24.3 g, 176.2 mmol) in 44 mL of DMF was stirred for 20 hours at room temperature. The reaction mixture was diluted with 300 mL of ether and washed with 250 mL of water and 5×100 mL of brine. The organic portion was dried ($MgSO_4$), filtered, and evaporated to give an oil, which was purified by flash column chromatography (silica gel, 90:10 hexane/ethylacetate) to give 2-isopropylanisole (a compound of Formula 2) (12.5 g, 82.1 mmol, 93%); $^1HNMR$ ($CDCl_3$) δ 1.2 (d, 6H), 3.3 (heptet, 1H), 3.8 (s, 3H), 6.8 (d, 1H), 6.88 (t, 1H), 7.13 (d, 1H), 7.2 (t, 1H).

Preparation of (2), varying $R^6, R^7, R^8, R^9$

In a similar manner, replacing 2-isopropylphenol with other compounds of Formula (1) and following the procedure described in Example 1 above, other compounds of Formula (2) are prepared.

EXAMPLE 2

Preparation of Compounds of Formula (3)

Preparation of (3) where $R^7$ is Isopropyl; and $R^6, R^8, R^9$ are H

To a suspension of potassium bromide (18.8 g, 157.7 mmol) in 400 mL of $CH_2Cl_2$ at 0° C. were added 18-Crown-6 (2.08 g, 7.88 mmol), 3-chloroperoxy benzoic acid (27.2 g, 157.7 mmol) and 2-isopropylanisole (a compound of Formula 1 from Example 1) (12.0 g, 78.8 mmol). After stirring for 3 hours at 0° C., the reaction mixture was poured into ice water (500 mL), and stirred for 30 minutes. The organic layer was separated, washed with saturated $NaHCO_3$ solution (400 mL), followed by water (300 mL), and dried ($MgSO_4$). The solvent was evaporated to give an oil, which was purified by flash column chromatography (silica gel, 98:2 hexane/ethylacetate) to give 13 g (56.7 mmol, 72%) of 4-bromo-2-isopropylanisole (a compound of Formula 3) as an oil; $^1HNMR$ ($CDCl_3$) δ1.2 (d, 6H), 3.3 (heptet, 1H), 6.7 (d, 1H), 6.84 (d, 1H), 7.29 (s, 1H).

Preparation of (3) varying $R^6, R^7, R^8, R^9$

In a similar manner, replacing 2-isopropylanisole with other compounds of Formula (2) and following the procedure described in Example 2 above, other compounds of Formula (3) are prepared.

EXAMPLE 3

Preparation of Compounds of Formula (5)

Preparation of (5) where $R^4$ is H; and $R^3, R^5$ are Methyl

A mixture of commercially available 4-bromo-3,5-dimethylphenol (a compound of Formula 4) (25.0 g, 124.3 mmol), methyl iodide (35.3 g, 248.6 mmol), and potassium carbonate (34.4 g, 248.6 mmol) in 62.5 mL of DMF was stirred for 2 hours at room temperature. The reaction mixture was diluted with 300 mL of ether and washed with 250 mL of water and 5×100 mL of brine. The organic portion was dried ($MgSO_4$), filtered, and evaporated to give an oil, which was purified by flash column chromatography (silica gel, 90:10 hexane/ethylacetate) to give 4-bromo-3,5-dimethylanisole (a compound of Formula 5) (26 g, 120.8 mmol, 97%); $^1HNMR$ ($CDCl_3$) δ2.39 (s, 6H), 3.76 (s, 3H), 6.67 (s, 2H).

Preparation of (5), varying $R^3, R^4, R^5$

In a similar manner, replacing 4-bromo-3,5-dimethylphenol with other compounds of Formula (4) and following the procedure described in Example 3 above, other compounds of Formula (5) are prepared.

EXAMPLE 4

Preparation of Compounds of Formula (6)

Preparation of (6) where $R^4$ is H; and $R^3, R^5$ are Methyl

To 4-bromo-3,5-dimethylanisole (a compound of Formula 5 from Example 3) (20 g, 93.0 mmol) in 500 mL of THF at −78° C. was added 120 mL of tert-Butyllithium (1.7 M in pentane). The reaction mixture was stirred for 30 minutes at −78° C. and then DMF (136.0 g, 186.0 mmol) was added. The reaction mixture was stirred for 1 hour at −78° C. and for 1.5 hours at room temperature, diluted with 300 mL of ether, washed with 300 mL of water, acidified 1N HCl, and 5×100 mL of brine. The organic portion was dried ($MgSO_4$), filtered, and evaporated to give the crude product, which was purified by flash column chromatography (silica gel, 90:10 hexane/ethylacetate) to yield 2,6-dimethyl-4-methoxybenzaldehyde (a compound of Formula 6), (9.50 g, 57.8 mmol, 62%) as a white solid; $^1HNMR$ ($CDCl_3$ δ2.61 (s, 6H), 3.83 (s, 3H), 6.6 (s, 2H), 10.5 (s, 1H).

Preparation of (6), varying $R^5$

In a similar manner, replacing 4-bromo-3,5-dimethylanisole with other compounds of Formula (5) and following the procedure described in Example 4 above, other compounds of Formula (6) are prepared.

EXAMPLE 5

Preparation of Compounds of Formula (7)

Preparation of (7) where $R^4, R^6, R^7, R^9$ are H; $R^3, R^5$ are Methyl; and $R^8$ is Isopropyl To 4-bromo-2-isopropylanisole (a compound of Formula 3 from Example 2) (12 g, 52.4 mmol) in 300 mL of THF at −78° C. was added 68 mL of tert-butyllithium (1.7 M in pentane). The reaction mixture was stirred for 10 min at −78° C. and then 2,6-dimethyl-4-methoxybenzaldehyde (a compound of Formula 6 from Example 4) (8.6 g, 52.4 mmol) was added. The reaction mixture was stirred for 1 hour at −78° C. and for 1.5 hours at room temperature, diluted with 150 mL of ether, washed with 150 mL of water, acidified with 1N HCl, and washed with 5×50 mL of brine. The organic portion was dried ($MgSO_4$), filtered, and evaporated to give the crude product, which was purified by flash column chromatography (silica gel, 95:5 hexane/ethylacetate) to yield 3,5-dimethyl-4-(3'-isopropyl-4'-methoxybenzylhydroxy) anisole (7) (12 g, 38.2 mmol, 73%) as an oil; $^1HNMR$ ($CDCl_3$) δ1.2 (dd, 6H), 2.27 (s, 6H), 3.30 (heptet, 1H), 3.80 (s, 6H), 6.26 (s, 1H), 6.59 (s, 2H), 6.76 (d, 1H), 6.89 (d, 1H), 7.24 (s, 1H).

Preparation of (7), varying $R^4, R^6, R^7, R^8, R^9$

In a similar manner, optionally replacing 4-bromo-2-isopropylanisole with other compounds of Formula (3), and optionally replacing 2,6-dimethyl-4-methoxybenzaldehyde with other compounds of Formula (6), and following the procedure described in Example 5 above, other compounds of Formula (7) are prepared.

EXAMPLE 6

Preparation of Compounds of Formula II

Preparation of II where $R^4, R^6, R^7, R^9$ are H; $R^3$¹ $R^5$ are Methyl; $R^8$ is Isopropyl; and $R^1$ is Ethoxy A solution of 3,5-dimethyl-4-(3'-isopropyl-4'-methoxybenzylhydroxy) anisole (a compound of Formula 7 from Example 5) (40 mg, 0.13 mmol) and ethanol (5.1 mmol) in $CH_2Cl_2$ (8 mL) was cooled to −45° C. (dry ice/acetonitrile bath). TFA (167 μL, 2.2 mmol) was added and the reaction stirred 2 h at −45° C. The reaction was quenched by adding sat. $NaHCO_3$ (5 mL) and water (5 mL). Layers were separated and the aqueous phase extracted twice with diethyl ether ("$Et_2O$") (7 mL). Combined extracts were washed with brine (10 ml), dried over $MgSO_4$ and evaporated to give the crude product, which was purified by flash chromatography (1:20 $Et_2O$-hexanes) to yield ethoxy-4,4'-dimethoxy-2,6-dimethyl-3'-(1-methylethyl) diphenylmethane (a compound of Formula II) (40 mg, 0.095mmol, 73%); $^1H$ NMR ($CDCl_3$) δ 7.17 (d, J=1.6 Hz, 1 H), 6.90 (dd, J=1.5, 8.4 Hz, 1 H), 6.71 (d, J=8.4Hz, 1 H),6.57 (s, 2 H), 5.80 (s, 1 H), 3.79 (s, 3 H), 3.78 (s, 3 H), 3.47 (br q, J=7.0 Hz, 2 H),3.26 (heptet, J=6.9 Hz, 1 H), 2.24 (s, 6 H), 1.26 (t, J=7.0 Hz, 3 H), 1.17 (d, J=6.7 Hz, 3 H), 1.15 (d, J=6.7 Hz, 3 H); HRMS exact mass calcd for $C_{22}H_{30}O_3$ 342.2195, found 342.2189.

Preparation of II, varing $R^1$ $R^1$ is ethylthio

Substitution of ethanethiol for ethanol in the above reaction and starting with 35 mg of the compound of Formula (7), with the additional step of quenching the reaction with 0.5 M NaOH (10 mL), and treating the extracted aqueous phase with bleach to reduce the stench, yielded ethylthio-4,4'-dimethoxy-2,6-dimethyl-3'-(1-methylethyl) diphenylmethane (a compound of Formula II) (33 mg, 0.098 mmol, 89%); $^1H$ NMR ($CDCl_3$) δ7.30 (d, J=2.0 Hz, 1 H), 7.05 (dd, J=1.6, 8.4 Hz, 1 H), 6.73 (d, J=8.5 Hz, 1 H), 6.56 (s, 2 H), 5.58 (s, 1 H), 3.79 (s, 3 H), 3.77 (s, 3 H), 3.27 (heptet, J=6.9 Hz, 1 H), 2.67—2.48 (M, 2 H), 2.23 (br s, 6 H), 1.28 (t, J=7.4 Hz, 3 H), 1.17 (app t, J=7.0 Hz, 6 H); HRMS exact mass calcd for $C_{22}H_{30}O_2S$ 358.1966, found 358.1953.

$R^1$ is phenylthio

Substitution of thiophenol for ethanol in the above reaction and starting with 41 mg (0.13 mmol) of the compound of Formula (7), with the additional step of quenching the reaction with 0.5 M NaOH (10 mL), and treating the extracted aqueous phase with bleach to reduce the stench, yielded 4,4'-dimethoxy-2,6-dimethyl-3'-(1-methylethyl) diphenylphenylthio methane (a compound of Formula II) (35 mg, 0.073 mmol, 66%); $^1H$ NMR ($CDCl_3$) δ 7.34 (s, 1 H), 7.32 (s, 1 H), 7.25–7.17 (m, 3 H), 7.08 (dd, J=1.7, 8.4 Hz, 1 H), 6.72 (d, J=8.5 Hz, 1 H), 6.55 (s, 2 H), 5.89 (s, 1 H), 3.79 (s, 3 H), 3.78 (s, 3 H), 3.26 (heptet, J=6.9 Hz, 1 H), 2.13 (br s, 6 H), 1.15 (d, J=6.9 Hz, 3 H), 1.09 (d, J=6.9 Hz, 3 H); HRMS exact mass calcd for $C_{26}H_{29}O_2S$ (M—H$^+$) 405.1888, found 405.1894.

$R^1$ is alkenyl

Substitution of allyltimethylsilane ($CH_2CHCH_2Si(CH_3)_3$) for ethanol in the above reaction and starting with 35 mg of the compound of Formula (7), yielded 4,4-[4',4"-dimethoxy-2',6'-dimethyl-3'-(1-methylethyl)diphenyl]butan-1-ene (a compound of Formula II) (41 mg, 0.12 mmol, 93%); $^1H$ NMR ($CDCl_3$) δ7.05 (d, J=1.7 Hz, 1 H), 6.87 (dd, J=1.6, 8.4 Hz, 1 H), 6.71 (d, J=8.5 Hz, 1 H), 6.54 (s, 2 H), 5.78—5.67 (m, 1 H), 5.09 (dd, J=1.0, 17.1 Hz, 1 H), 4.93 (d, J=10.2 Hz, 1 H), 4.50 (t, J=7.9 Hz, 1 H), 3.78 (s, 3 H), 3.77 (s, 3 H), 3.26 (heptet, J=6.9 Hz, 1 H), 3.09—3.00 (m, 1 H), 2.80—2.70 (m, 1H), 2.15 (br s, 6 H), 1.16 (d, J=7.1 Hz, 3 H), 1.14 (d, J=7.1 Hz, 3H); HRMS exact mass calcd for $C_{23}H_{30}O_2$ 338.2246, found 338.2247.

$R^1$ is a substituted aryl such as 2,4-dimethoxyphenyl

Substitution of 1,3-dimethoxybenzene for ethanol in the above reaction, yielded 4,4',2",4"-tetamethoxy-2,6-dimethyl-3'-(1-methylethyl)triphenylmethane (a compound of Formula II) (90% yield); $^1H$ NMR ($CDCl_3$) δ6.85 (s, 1 H), 6.76 (d, J=8.4 Hz, 1 H), 6.68 (s, 1 H), 6.54 (s, 2 H), 6.47 (d, J=2.2 Hz, 1 H), 6.36 (dd, J=2.3, 8.5 Hz, 1 H), 5.93 (s, 1 H), 3.79 (s, 3 H), 3.78 (s, 3 H), 3.77 (s, 3 H), 3.67 (s, 3 H), 3.24 (heptet, J=6.9 Hz, 1 H), 1.99 (s, 6 H), 1.09 (d, J=6.9 Hz, 6 H); HRMS exact mass calcd for $C_{28}H_{34}O_4$ 434.2457, found 434.2458.

Preparation of II, varying $R^4, R^6, R^7, R^9$

In a similar manner, replacing 3,5-dimethyl-4-(3'-isopropyl-4'-methoxybenzylhydroxy) anisole with other compounds of Formula (7), and following the procedure described in Example 6 above, other compounds of Formula II are prepared.

EXAMPLE 7

Preparation of Compounds of Formula (15)

Preparation of (15) where $R^4$, $R^6,R^7,R^9$ are H; $R^3$, $R^5$ are Methyl; $R^8$ is Isopropyl; $R^1$ is Ethoxy To ethoxy-4-[(1,1-dimethylethyl)methoxyphenylsilyloxy]-2,6-dimethyl-4'-tris(1-methylethyl)silyloxy-3'-(1-methylethyl)diphenylmethane (a compound of Formula III) is added anhydrous $CH_2Cl_2$. The reaction mixture is cooled to −78° C. and 1.0 eq. TBAF is added via syringe. The reaction is allowed to warm slowly and is stirred. The reaction mixture is then washed with saturated ammonium chloride and the aqueous phase extracted with $Et_2O$. The combined organic layers are washed with brine, dried ($MgSO_4$), and evaporated to give the crude product. Purification by flash chromatography (silica gel, 1:9 ethyl acetate:hexanes) gives ethoxy-4-hydroxy-2,6-dimethyl-4'-tris(1-methylethyl)silyloxy-3'-(1-methylethyl)diphenylmethane (a compound of Formula 15).

Preparation of (15), varying $R^1,R^4,R^6,R^7,R^8,R^9$

In a similar manner, replacing ethoxy-4-[(1,1-dimethylethyl)methoxyphenylsilyloxy]-2,6-dimethyl-4'-tris(1-methylethyl)silyloxy-3'-(1-methylethyl) diphenylmethane with other compounds of Formula III, and following the procedure described in Example 7 above, other compounds of Formula (15) are prepared.

EXAMPLE 8

Preparation of Compounds of Formula (16)

Preparation of (16) where $R^4,R^6,R^7,R^9$ are H: $R^3,R^5$ are Methyl: $R^8$ is Isopropyl: $R^1$ is Ethoxy To ethoxy-4-hydroxy-2,6-dimethyl-4'-tris(1-methylethyl)silyloxy-3'-(1-methylethyl)diphenylmethane (a compound of Formula 15 from Example 7), is added DMF, 2 eq. $Cs_2CO_3$ and 1.5 eq. ethylbromoacetate. The reaction is stirred, then mixed with a saturated ammonium chloride solution and extracted with $Et_2O$. The combined organics are dried ($MgSO_4$) and evaporated to give the crude product, ethoxy-4-ethyloxyacetate-2,6-dimethyl-4'-tris(1-methylethyl)silyloxy-3'-(1-methylethyl)diphenylmethane (a compound of Formula 16).

Preparation of (16), varying $R^1,R^4,R^6,R^7,R^8,R^9$

In a similar manner, replacing ethoxy-4-hydroxy-2,6-dimethyl-4'-tris(1-methylethyl)silyloxy-3'-(1-methylethyl) diphenylmethane with other compounds of Formula (15), and following the procedure described in Example 8 above, other compounds of Formula (16) are prepared.

EXAMPLE 9

Preparation of Compounds of Formula (17)

Preparation of (17) where $R^4,R^6,R^7,R^9$ are H; $R^3,R^5$ are Methyl; $R^8$ is Isopropyl; $R^1$ is Ethoxy To ethoxy-4-ethyloxyacetate-2,6-dimethyl-4'-tris(1-methylethyl)silyloxy-3'-(1-methylethyl)diphenylmethane (a compound of Formula 16 from Example 8) is added methanol, 2 eq. lithium hydroxide monohydrate and 1 eq. water. The reaction is stirred, then the solvent volume is reduced by evaporation. The residue is suspended in a saturated ammonium chloride solution and extracted with Et$_2$O. The combined organics are dried (MgSO$_4$) and evaporated to give the crude product, ethoxy-2,6-dimethyl-4'-tris (1-methylethyl)silyloxy-3'-(1-methylethyl) diphenylmethane-4-oxyacetic acid (a compound of Formula 17).

Preparation of (17), varying R$^1$,R$^4$, R$^6$,R$^7$,R$^8$,R$^9$

In a similar manner, replacing ethoxy-4-ethyloxyacetate-2,6-dimethyl-4'-tris(1-methylethyl)silyloxy-3'-(1-methylethyl)diphenylmethane with other compounds of Formula (16), and following the procedure described in Example 9 above, other compounds of Formula (17) are prepared.

EXAMPLE 10

Preparation of Compounds of Formula I
Preparation of I where n is 1; R$^4$,R$^6$,R$^7$,R$^9$,R$^{10}$ are H; R$^3$,R$^5$ are Methyl; R$^8$ is Isopropyl; R$^1$ is Ethoxy Ethoxy-2,6-dimethyl-4'-tris(1-methylethyl)silyloxy-3'-(1-methylethyl)diphenylmethane-4-oxyacetic acid (a compound of Formula 17 from Example 9) is dissolved in an equal mixture of acetonitrile and CH$_2$CH$_2$. 18-Crown-6 (0.5 eq.) and potassium fluoride (1.1 eq.) are added and the reaction mixture is stirred for 15 hours. The solvent volume is reduced by evaporation and the residue is suspended in a saturated ammonium chloride solution and extracted with CHCl$_3$. The combined organics are dried (MgSO$_4$) and evaporated to give the crude product. Reverse phase (C18) HPLC (water/acetonitrile+0.1% TFA) gives the pure product, ethoxy-2,6-dimethyl- 4'-hydroxy-3'-(1-methylethyl)diphenylmethane-4-oxyacetic acid (a compound of Formula I).

Preparation of I, varying n, R$^1$,R$^4$,R$^6$,R$^7$,R$^8$,R$^9$,R$^{10}$

In a similar manner, replacing ethoxy-2,6-dimethyl-4'-tris (1-methylethyl)silyloxy-3'-(1-methylethyl) diphenylmethane-4-oxyacetic acid with other compounds of Formula (17), and following the procedure described in Example 10 above, other compounds of Formula I are prepared.

EXAMPLE 11

Preparation of Compound (I-1), a Compound of Formula I
Preparation of a Compound of Formula (9)

To a stirred, chilled (0° C.) solution of commercially available 2isopropyl phenol (30.0 g, 220 mmol) in anhydrous methylene chloride (250 ml), elemental bromine (10 ml, 19 mmol) was added. After stirring for 1 hr. at 0° C., the reaction was quenched with NH$_4$OH (50 ml), water (250 ml) and saturated NaHCO$_3$ (200 ml). The aqueous phase was extracted with diethyl ether and combined organic fractions were washed with brine and dried (MgSO$_4$), followed by filtration; solvent was removed by rotary evaporation to yield a golden oil (42 g). $^1$H NMR analysis indicated only ~75% reaction, thus the crude product was subjected to the same reaction conditions with only 2.8 ml (54 mmol) of bromine added, which yielded a golden oil (50.6 g). Purification by column chromatography (4"×7", 5% →20% EtOAc/Hexanes) yielded 4-bromo-2-isopropylphenol (a compound of Formula 9) as a colorless oil (30 g, 63%). $^1$H NMR (600 MHz, CDCl$_3$) δ7.28 (d, J=2.6 Hz, 1 H), 7.15 (dd, J=8.4, 2.2 Hz, 1 H), 6.63, (d, J=8.4 Hz, 1 H), 4.79 (s, 1 H), 3.17 (heptet, J=6.9 Hz, 1 H), 1.24 (d, J=7.0 Hz, 6H)

Preparation of a Compound of Formula (10)

To a stirred solution of TIPS chloride (12 ml, 56 mmol) in anhydrous 1,2-dichloroethane (70 ml) was added 4-bromo-2-isopropylphenol (a compound of Formula 9) (9.6 g, 46 mmol) and imidazole (7.8 g, 114 mmol). Reaction was refluxed from 30 min, then allowed to stir overnight at room temperature. Reaction was refluxed 1 hour further, then 150 ml of 0.6 M HCl was added, layers separated and the aqueous phase extracted with diethyl ether. Combined organic fractions were washed with saturated NaHCO$_3$, dried (MgSO$_4$), filtered through a Celite plug and solvent was removed by rotary evaporation to yield an oil (18.3 g). Purification by fractional distillation (bp 137° C., 0.3 mm) yielded 3-isopropyl-4-triisopropylsilyoxy-bromobenzene (a compound of Formula 10) as a white solid (12.3 g, 72%).$^1$H NMR (600 MHz, CDCl$_3$) δ7.27 (d, J=2.6 Hz, 1 H), 7.11 (dd, J=8.4, 2.6 Hz, 1 H), 6.64 (d,J=8.8 Hz, 1 H), 3.33 (heptet, J=6.8 Hz, 1 H), 1.30 (heptet, J=7.5 Hz, 3 H), 1.19 (d, J=6.6 Hz, 6 H), 1.10 (d, J=7.7 Hz, 18 H).

Preparation of a Compound of Formula (12)

To a stirred solution of commercially available 4-bromo-3,5-dimethylphenol (a compound of Formula 11, 13.5 g, 66.9 mmol) and imidazole (11.4 g, 167 mmol) in anhydrous methylene chloride (125 ml) was added tert-butylmethoxyphenylsilyl bromide (19.2 g, 70.3 mmol). Reaction was stirred 2.5 hr., then 200 ml 0.1 M HCl was added and the layers were separated. The aqueous layer was extracted with diethyl ether, and the combined organic fractions were washed with brine and dried (MgSO$_4$). Removal of drying agent by filtration and solvent by rotary evaporation yielded 4-TBMPS-2,6-dimethylbromobenzene (a compound of Formula 12), as a golden oil (26.6 g, 100%) which was used without further purification. $^1$H NMR (600 MHz, CDCl$_3$) δ 7.66 (d, J=7.3 Hz, 2 H), 7.44 (t, J=8.8 Hz, 1 H), 7.39 (t, J=7.5 IS Hz, 2 H), 6.73 (s, 2 H), 3.61 (s, 3 H), 2.33 (s, 6 H), 0.99 (s, 9 H).

Preparation of a Compound of Formula (13)

To a solution of 4-TBMPS-2,6-dimethylbromobenzene (a compound of Formula 12) (26.2 g, 66.6 mmol) in anhydrous THF cooled to −78° C. was added a solution of butyllithium in hexanes (2.5M, 76.6 mmol) over several min. Anhydrous DMF (7.7 ml, 99.9 mmol) was then added over 5 min. After stirring 50 minutes at −78° C., 250 ml 0.2M HCl was added and the mixture extracted with diethyl ether. The organic fractions were washed with brine and dried (MgSO$_4$). Filtration followed by rotary evaporation yielded a green syrup. Column chromatography (4"×7", 10% →20% ether/hexanes yielded a benzaldehyde (a compound of Formula 13), as a white solid (16.3 g, 71%). $^1$H NMR (600 MHz, CDCl$_3$) δ10.47 (s, 1 H), 7.66 (d, J=7.3 Hz, 2 H), 7.45 (t, J=7.0 Hz, 1 H), 7.40 (t, J=7.3 Hz, 2 H), 6.69 (s, 2 H), 3.64 (s, 3 H), 2.55 (s, 6 H), 1.01 (s, 9 H).

Preparation of a Compound of Formula (14) from compounds of Formulas (10) and (13)

To a stirred solution of 3-isopropyl-4-triisopropylsilyoxy-bromobenzene (a compound of Formula 10) (11.0 g, 29.6 mmol) in anhydrous THF (125 ml) at −78° C. was added solution of butyllithium in hexanes (2.5M, 32.3 mmol). This mixture was transferred via cannula to a stirred suspension of cerous chloride (7.96 g, 32.3 mmol) in anhydrous THF (150 ml) at −78° C. After stirring 30 min. at −78° C., the benzaldehyde (a compound of Formula 13) (9.21 g, 26.9 mmol) in anhydrous THF (25 ml) was added via cannula. After a further 90 min. at −78° C., dilute HCl (170 ml, 0.3M) was added and the mixture extracted with diethyl ether. Combined organic fractions were washed with a mixture of brine and saturated NaHCO$_3$, then dried (MgSO$_4$) and filtered through a Celite plug. Removal of solvent by rotary evaporation yielded a benzyl alcohol (a compound of Formula 14) as a yellow syrup (20.7 g) which was used directly in the next reaction.

Preparation of a Compound of Formula III

To a stirred solution of the crude benzyl alcohol (a compound of Formula 14) (20.6 g) and anhydrous methanol (10.9 ml, 269 mmol) in anhydrous methylene chloride (400 ml) at −45° C. (dry ice/acetonitrile slush) was added TFA (10.4 ml, 135 mmol). After stirring 50 min. at −45° C., reaction was quenched with 230 ml of a mixture of brine, saturated $NaHCO_3$ and water (9:9:4). Layers were separated and the aqueous phase extracted with diethyl ether. Combined organic fractions were dried ($MgSO_4$), filtered through Celite and solvent removed by rotary evaporation to yield an orange oil (20.5 g). Column chromatography (silica gel, 4"×7", 0%→15% ether/hexanes) yielded a methyl ether (a compound of Formula III) as a yellow syrup (14.8 g, 77% yield from the benzaldehyde, a compound of Formula 13). $^1$H NMR (600 MHz, $CDCl_3$) δ 7.70 (d, J=6.6 Hz, 2 H), 7.43 (t, J=7.0 Hz, 1 H), 7.39 (t, J=7.1 Hz, 2 H), 7.04 (s, 1 H), 6.78 (d, J=8.1 Hz, 1 H), 6.67 (s, 2 H), 6.64 (d, J=8.4 Hz, 1 H), 5.69 (s, 1 H), 3.62 (s, 3 H), 3.31 (app. s, 4 H), 2.17 (s, 6 H), 1.28 (heptet, J=7.5 Hz, 3 H), 1.13 (d, J=7.0 Hz, 3 H), 1.11 (d, J=3.7 Hz, 3 H), 1.09 (d, J=7.3 Hz, 18 H), 1.00 (s, 9 H).

Preparation of a Compound of Formula (15)

To a stirred solution of the methyl ether (a compound of Formula III) (4.03 g, 6.2 mmol) in anhydrous THF (60 ml) was added triethylamine trihydrofluoride (2.02 ml, 12.4 mmol). After 45 min., reaction mixture was partitioned between saturated $NaHCO_3$ and diethyl ether. The aqueous layer was further extracted with ether and combined organic fractions were dried ($MgSO_4$), then filtered through a Celite plug, and solvent was removed by rotary evaporation to yield a yellow syrup (4.1 g) which crystallized upon further standing. Recrystallization, first from hexanes, then 1:3 ether:hexanes yielded a phenol (a compound of Formula 15), as a white solid (2.40 g, 85%). $^1$H NMR (300 MHz, $CDCl_3$) δ7.15 (s, 1 H), 6.73 (dd, J=8.1, 1.2 Hz, 1 H), 6.64 (d, J=8.3 Hz, 1 H), 6.51 (s, 2 H), 5.70 (s, 1 H), 4.68 (br. s, 1 H), 3.32 (app. s, 4 H), 2.20 (s, 6 H), 1.25 (heptet, J=7.3 Hz, 3 H), 1.15 (app. t, J=6.8 Hz, 6 H), 1.08 (d, J=7.2 Hz, 18 H).

Preparation of Compound (16-1)

To a stirred solution of the phenol (a compound of Formula 15) (2.78 g, 6.08 mmol) in anhydrous DMF (10 ml), was added methyl bromoacetate (864μL, 9.13 mmol) and potassium carbonate (1.69 g, 12.2 mmol). Reaction was quenched after 6 hr. by slow addition of dilute HCl (1M, 30 ml). The mixture was diluted with 150 ml water and extracted with diethyl ether. Combined organic fractions were washed twice with brine, then dried ($MgSO_4$), filtered through a Celite plug and solvent removed by rotary evaporation to yield a methyl ether as a pale yellow oil (3.7 g, 100%). $^1$H NMR (300 MHz, $CDCl_3$) δ7.15 (d, J=0.9 Hz, 1 H), 6.71 (dd, J=8.3, 1.6 Hz, 1 H), 6.63 (d, J=8.4 Hz, 1 H), 6.57 (s, 2 H), 5.70 (s, 1 H), 4.63 (s, 2 H), 3.82 (s, 3 H), 3.32 (app. s, 4 H), 2.22 (s, 6 H), 1.26 (heptet, J=7.3 Hz, 3 H), 1.15 (app. t, J=6.5 Hz, 6 H), 1.09 (d, J=7.2Hz, 18H).

To a stirred, solution of the methyl ether (2.0 g, 3.8 mmol), allyltimethylsilane (15 ml, 95 mmol) in anhydrous methylene chloride (50 ml) cooled to −45° C. (dry ice/acetonitrile slush), was added TFA (2.9 ml, 38 mmol). After stirring 15 min. at −45 ° C., reaction was quenched with 50 ml of saturated $NaHCO_3$. The aqueous layer was extracted with diethyl ether and combined organic fractions were dried ($MgSO_4$), filtered through a Celite plug and solvent removed by rotary evaporation to yield a cloudy tan syrup (1.92 g). Column chromatography (silica, 1.5"×5",10% EtOAc/hexanes yielded the alkene, Compound (16-1) (1.68 g, 80%).

Preparation of Compound (18)

To a stirred solution of Compound (16-1), (1.68 g, 3.12 mmol) in anhydrous THF (40 ml), cooled on an ice bath, was added borane (1.0M in THF, 3.12 mmol). Reaction was allowed to warm to room temperature and stirred 4.5 hr. Additional borane (0.6 mmol) was added to drive hydroboration to completion, and reaction was stirred an additional 3 hr. Hydrogen peroxide (318μl, 3.12 mmol) and NaOH (1M, 0.94 mmol) diluted in water (3 ml) were then added, and the reaction was stirred 20 min. Saturated $NH_4Cl$ was then added, layers separated, and the aqueous phase was extracted with diethyl ether. Combined organic fractions were washed with brine and dried ($MgSO_4$), filtered through Celite and solvent removed by rotary evaporation to yield the crude product (1.81 g). Column chromatography (silica, 1"×5",20%→35% EtOAc/hexanes) yielded the alcohol, Compound (18) (836 mg, 48%). $^1$H NMR (600 MHz, $CDCl_3$) δ7.00 (s, 1 H), 6.70 (d, J=8.4 Hz, 1 H), 6.63 (d, J=8.1 Hz, 1 H), 6.53 (br. s, 2 H), 4.60 (s, 2 H), 4.40 (t, J=7.7 Hz, 1 H), 3.81 (s, 3 H), 3.66 (heptet, J=6.4 Hz, 1 H), 3.33 (t, J=6.8 Hz, 2 H), 2.12 (br. s, 6 H), 2.37—2.32 (m, 1 H), 2.06—1.99 (m, 1 H), 1.65—1.58 (m, 1 H), 1.45—1.38 (m, 1 H), 1.28 (heptet, J=7.5 Hz, 3 H), 1.15 (d, J=6.9 Hz, 3 H), 1.12 (d, J=7.0 Hz, 3 H), 1.09 (d, J=7.3 Hz, 18 H).

Preparation of Compound (19)

To a stirred suspension of Compound (18), (655 mg, 116 mmol), potassium bromide (14 mg, 0.12 mmol) and TEMPO in methylene chloride (10 ml), cooled to 0° C., was slowly added a mixture of sodium hypochlorite solution (1.87 ml, 1.39 mmol) and saturated sodium bicarbonate (2 ml). After 40 min., 10 ml of 10% HCl containing potassium iodide (125 mg) was added and the aqueous layer extracted with diethyl ether. Combined organic phases were washed with 10% sodium thiosulfate and 1:1 brine:water, then dried ($MgSO_4$), filtered through Celite and solvent removed by rotary evaporation to yield the aldehyde, Compound (19), as a yellow oil (615 mg, 96%). $^1$H NMR (600 MHz, $CDCl_3$) δ9.71 (s, 1 H), 6.99 (s, 1 H), 6.71 (d, J=6.2 Hz, 1 H), 6.64 (d, J=7.1 Hz, 1 H), 6.55 (s, 2 H), 4.60 (s, 2 H), 4.42–4.40 (m, 1 H), 3.82 (s, 3 H), 3.33 (heptet, J=7.0 Hz, 1 H), 2.64—2.58 (m, 1 H), 2.47—2.41 (m, 1 H), 2.35—2.29 (m, 2 H), 2.13 (br. s, 6 H), 1.28 (heptet, J=7.4 Hz, 3 H), 1.16 (d, J=7.0Hz, 3 H), 1.12 (d, J=7.0 Hz, 3 H), 1.09 (d, J=7.3 Hz, 18H).

Preparation of Compound (21)

To a stirred suspension of commercially available 8-bromooctanoic acid, Compound (20), (1.27 g, 5.69 mmol) and HBTU (2.16 g, 5.69 mmol) in anhydrous methylene chloride (20 ml) was added N-methylbutylamine (673 μl, 5.69 mmol) and triethylamine (1590 μl, 11.4 mmol). After 4 hr., brine was added and the aqueous phase extracted with diethyl ether. The combined organic fractions were washed with 1M HCl (3×20 ml), saturated $NaHCO_3$ (2×20 ml) and brine, then dried ($MgSO_4$), filtered through Celite and solvent removed by rotary evaporation. Column chromatography (silica gel, 1.5"×5", 20%→30% EtOAc/Hexanes) yielded the bromooctamide, Compound (21), as a colorless oil (1.219 g, 76%). $^1$H NMR (600 MHz, $CDCl_3$) δ3.40 (t, J=7.0 Hz, 2 H), 3.36 (t, J=7.3 Hz, 1 H), 3.25 (t, J=7.3 Hz, 1 H), 2.97 (s, 1.5 H), 2.91 (s, 1.5 H), 2.29 (app. q, J=7.4 Hz, 2 H), 1.86 (quintet, J=7.1 Hz, 2 H), 1.66—1.62 (m, 2 H), 1.54 (quintet, J=7.4 Hz, 1 H), 1.49 (quintet, J=7.5 Hz, 1 H), 1.46—1.42 (m, 2 H), 1.36—1.28 (m, 6 H), 0.96 (t, J=7.3 Hz, 1.5 H), 0.92 (t, J=7.3Hz, 1.5 H).

Preparation of Compound (22)

To undiluted Compound (21) (117 mg, 0.400 mmol) was added triphenylphosphine (105 mg, 0.400 mmol). The mixture was stirred at 125° C. for 22 hr., then cooled and dissolved in anhydrous THF (4 ml). To this solution was added potassium tert-butoxide (45 mg, 0.400 mmol) and then aldehyde 19 (200 mg, 0.36 mmol), dissolved in anhydrous THF. Reaction was heated to reflux for 7 hr., then quenched with saturated NH$_4$Cl and the aqueous phase extracted with diethyl ether. Combined organic fractions were washed with brine, dried (MgSO$_4$) filtered through a Celite pad and solvent removed by rotary evaporation. This procedure was repeated once and the crude products chromotographed twice under different conditions (silica gel, 1"×6", 10%→35% EtOAc/Hexanes) (silica gel, 0.5"× 7"0.2.5%→20% EtOAc/Methylene chloride) to yield the alkene, Compound (22), as a colorless oil (79 mg, 13%).

Preparation of Compound (23)

To a stirred solution of Compound (22) (29 mg, 0.039 mmol) in absolute ethanol was added palladium on carbon (spatula tip). The flask was purged with hydrogen gas (balloon) and stirred 24 hr. under balloon pressure. Filtration through Celite and rotary evaporation yielded the ester, Compound (23) (25.5 mg, 87%). $^1$H NMR (600 MHz, CDCl$_3$) δ6.98 (s, 1 H), 6.70 (d, J=8.4 Hz, 1 H), 6.62 (d, J=8.4 Hz, 1 H), 6.53 (br. s, 2 H), 4.60 (s, 2 H), 4.37—4.34 (m, 1 H), 3.81 (s, 3 H), 3.37—3.30 (m, 2 H), 3.25 (t, J=7.5 Hz, 1 H), 2.96 (s, 1.5 H), 2.90 (s, 1.5 H), 2.30—2.26 (m, 2 H), 2.25—2.21 (m, 1 H), 2.04 (br. s, 6 H), 1.95—1.89 (m, 1 H), 1.64—1.60 (m, 2 H), 1.57—1.52 (m, 1 H), 1.51—1.46 (m, 1 H), 1.35—1.24 (m, 19 H), 1.15 (d, J=7.0Hz, 3 H), 1.12 (d, J=7.0Hz, 3 H), 1.09 (d, J=7.3 Hz, 18 H), 0.96—0.91 (m, 3 H).

Preparation of Compound (24)

To a stirred solution of Compound (23) (25.5 mg, 0.034 mmol) in anhydrous THF (500 µl) was added triethylamine trihydrofluoride (552 µl, 3.4 mmol). After 18 hr., reaction was quenched with potassium carbonate (700 mg, 5.1 mmol) and water (3 ml), then extracted with ethyl acetate. Combined organic fractions were dried (MgSO$_4$), filtered through Celite and solvent removed by rotary evaporation. Column chromatography (silica gel, 0.5"×6"0.10% EtOAc/ Hexanes→20% EtOAc/1% MeOH/Hexanes) yielded the phenol, Compound (24), (12 mg, 59%) and unreacted starting material (9.5 mg).

Preparation of Compound (I-1)

To a stirred solution of Compound (24) (12 mg, 0.020 mmol) in methanol (1 ml) was added lithium hydroxide monohydrate (2 mg, 0.05 mmol) and water (2µl, 0.11 mmol). After 16 hr., saturated NH$_4$Cl and two drops of 1M HCl were added and the mixture was extracted with ethyl acetate. The combined organic fractions were dried (MgSO$_4$), filtered through Celite and solvent removed by rotary evaporation to yield the oxyacetic acid, Compound (1–5) (6 mg, 52%). $^1$H NMR (600 MHz, CDCl$_3$) δ7.00 (s, 1 H), 6.75 (d, J=7.3 Hz, 1 H), 6.61 (d, J=8.1 Hz, 1 H), 6.56 (br. s, 2 H), 4.62 (s, 2 H), 4.38—4.35 (m, 1 H), 3.37 (t, J=7.5 Hz, 1 H), 3.26 (t, J=7.5 Hz, 1 H), 3.16 (heptet, J=7.1 Hz, 1 H), 2.98 (s, 1.5 H), 2.93 (s, 1.5 H), 2.36—2.22 (m, 2 H), 2.21—2.15 (m, 1 H), 2.10 (br. s, 6 H), 2.05—1.96 (m, 1 H), 1.63—1.57 (m, 2 H), 1.56—1.52 (m, 1 H), 1.52—1.47 (m, 1 H), 1.37—1.29(m, 4 H), 1.28—1.23 (m, 4 H), 1.21 (app. d, J=7.0 Hz, 6 H), 1.18 (app. d, J=7.0 Hz, 4 H), 1.15—1.11 (m, 4 H), 0.95 (t, J=7.5 Hz, 1.5 H), 0.92 (t, J=7.3 Hz, 1.5 H).

HRMS exact mass calcd for C$_{36}$H$_{55}$NO$_5$:581.4080, found: 581.4082.

EXAMPLE 12

Preparation of Compound (I-2), a Compound of Formula I

Preparation of Compound (25)

To a stirred solution of Compound (22) (50 mg, 0.067 mmol, from Example 11) in anhydrous THF (1 ml) was added triethylamine trihydrofluoride (1.09 ml, 6.67 mmol). After 13 hr., reaction was quenched with potassium carbonate (1.28 g) and water (5 ml) and extracted with chloroform. Combined organic fractions were dried (MgSO$_4$), filtered through Celite, and solvent was removed by rotary evaporation. Column chromatography (silica, 0.5"×7", 10% EtOAc/CH$_2$Cl$_2$→15% EtOAc/3% MeOH/CH$_2$Cl$_2$) yielded the phenol, Compound (25) (33 mg, 83%). $^1$H NMR (600 MHz, CDCl$_3$) δ6.99 (s, 1H), 6.74 (d, J=7.3 Hz, 1 H), 6.67 (d, J=8.1 Hz, 1 H), 6.52 (s, 2 H), 6.05 (br. s, 1 H), 5.40—5.35 (m, 2 H), 4.59 (s, 2 H), 4.36 (t, J=7.3 Hz, 1 H), 3.81 (s, 3 H), 3.37 (t, J=7.5 Hz, 1 H), 3.26—3.19 (m, 2 H), 2.96 (s, 1.5 H), 2.92 (s, 1.5 H), 2.40—2.32 (m, 1 H), 2.28 (app. q, J=8.1 Hz, 2 H), 2.15 (br. s, 6 H), 2.13—2.09 (m, 1 H), 1.92—1.87 (m, 1 H), 1.86—1.81 (m, 2 H), 1.66—1.47 (m, 3 H), 1.35—1.27 (m, 4 H), 1.26—1.22 (m, 2 H), 1.21 (d, J=7.0 Hz, 3 H), 1.18 (d, J=6.6 Hz, 3 H), 1.16—1.14 (m, 1 H), 1.09 (app. d, J=7.3 Hz, 3 H), 0.95 (t, J=7.5 Hz, 1.5 H), 0.92 (t, J=7.3 Hz, 1.5 H).

Preparation of Compound (I-2)

To a stirred solution of Compound (25) (10 mg, 0.017 mmol) in methanol was added lithium hydroxide monohydrate (3 mg, 0.07 mmol) and water (1.7 µl, 0.093 mmol). After 26 hr., solvent was evaporated and the residue resuspended in saturated NH$_4$Cl and a drop of 1M HCl., which was extracted with ethyl acetate. Combined organic fractions were dried (MgSO$_4$), filtered through Celite, and solvent was removed by rotary evaporation to yield the oxyacetic acid, Compound (I-2) (7 mg, 71%). $^1$H NMR (600 MHz, CDCl$_3$) δ7.01 (s, 1 H), 6.74 (d, J=7.7 Hz, 1 H), 6.62 (d, J=8.4 Hz, 1 H), 6.56 (s, 2 H), 5.46—5.41 (m, 1 H), 5.36—5.32 (m, 1 H), 4.63 (s, 2 H), 4.38—4.36 (m, 1 H), 3.38 (t, J=7.5 Hz, 1 H), 3.26 (t, J=7.3 Hz, 1 H), 3.17 (heptet, J=6.6 Hz, 1 H), 2.99 (s, 1.5 H), 2.94 (s, 1.5 H), 2.38—2.30 (m, 2 H), 2.10 (br. s, 6 H), 2.06—1.95 (m, 2 H), 1.94—1.86 (m, 1 H), 1.75—1.68 (m, 2 H), 1.53—1.47 (m, 1 H), 1.36—1.28 (m, 3 H), 1.26 (app. s, 1 H), 1.21—1.18 (m, 9 H), 1.16—1.11 (m, 3 H), 0.96—0.91 (m, 3 H).

HRMS exact mass calculated for C$_{36}$H$_{53}$NO$_5$:579.3924, found: 579.3924.

EXAMPLE 13

Preparation of Compound (I-3), a Compound of Formula I

Preparation of Compound (26)

To a stirred solution of the phenol (compound of Formula 15 from Example 11) (2.32 g, 4.93 mmol) in anhydrous DMF (100 ml) was added cesium carbonate (3.21 g, 9.86 mmol) and ethyl bromoacetate (819 µl, 7.39 mmol). Reaction was stirred 3 hr., then quenched with 150 ml saturated NH$_4$Cl, then diluted with water (300 ml). Extraction with diethyl ether, followed by drying (MgSO$_4$), filtration and rotary evaporation yielded an oil (3.0 g). This contained some residual DMF, which was removed by partitioning the residue between ether and water to yield 2.82 g of a methyl ether. $^1$H NMR (600 MHz, CDCl$_3$) δ7.14 (s, 1 H), 6.71 (d, J=8.0 Hz, 1 H), 6.63 (d, J=8.4 Hz, 1 H), 6.58 (s, 2 H), 5.70 (s, 1 H), 4.61 (s, 2 H), 4.29 (q, J=7.1 Hz, 2 H), 3.32 (app. s, 4 H), 2.22 (s, 6 H), 1.32—1.25 (m, 6 H), 1.16 (d, J=7.0 Hz, 3 H), 1.15 (d, J=6.6Hz, 3 H), 1.09 (d, J=7.3 Hz, 18 H).

To a stirred solution of the methyl ether, (1.05 g, 1.93 mmol) and allyltrimethylsilane (13.2 ml, 83.3 mmol) in anhydrous methylene chloride (50 ml), chilled to −45° C. (dry ice/acetonitrile slush), was added TFA (2.1 ml, 28 mmol). After 20 min. at −45° C., cold bath was removed, and the reaction was quenched with 50 ml saturated NaHCO$_3$. The aqueous phase was extracted with diethyl ether, and the combined organic fractions were dried (MgSO$_4$), filtered, and solvent was removed by rotary evaporation. Column chromatography (silica, 1.5"×7", 7%→12% EtOAc/Hexanes) yielded the alkene, Compound (26) as a colorless oil (795 mg, 75%). $^1$H NMR (600 MHz, CDCl$_3$) δ7.01 (s, 1 H), 6.70 (d, J=8.1 Hz, 1 H), 6.63 (d, J=8.4 Hz, 1 H), 6.53 (s, 2 H), 5.72—5.68 (m, 1 H), 5.07 (d, J=16.9 Hz, 1 H), 4.92 (d, J=10.3 Hz, 1 H), 4.58 (s, 2 H), 4.49 (t, J=7.9 Hz, 1 H), 4.28 (q, J=7.1 Hz, 2 H), 3.33 (heptet, J=7.0 Hz, 1 H), 3.04—2.99 (m, 1 H), 2.74—2.69 (m, 1 H), 2.12 (br. s, 6 H), 1.30—1.25 (m, 6 H), 1.15 (d, J=7.0 Hz, 3 H), 1.12 (d, J=7.0 Hz, 3 H), 1.09 (d, J=7.3 Hz, 18 H).

Preparation of Compound (I-3)

To a stirred solution of Compound (26) (100 mg, 0.181 mmol) in anhydrous THF (5 ml) was added triethylamine trihydrofluoride (2 ml, 12 mmol). After 39 hr., reaction was quenched with 20 ml saturated NaHCO$_3$ and extracted with diethyl ether. Combined organic fractions were dried (MgSO$_4$), filtered, and solvent was removed by rotary evaporation. Column chromatography (silica, 0.5"×5|, 10%→14% EtOAc/Hexanes) yielded a phenol (57 mg, 79%).

To a stirred solution of the phenol (57 mg, 0.14 mmol) in methanol (3 ml) was added lithium hydroxide monohydrate (13 mg, 0.32 mmol) and water (14 μl, 0.79 mmol). After 13 hr., solvent was removed by rotary evaporation, and the residue was resuspended in saturated NH$_4$Cl, plus two drops of 1M HCl., and extracted with chloroform. Combined organic fractions were dried (MgSO$_4$), filtered, and solvent was removed by rotary evaporation to yield the oxyacetic acid, Compound (I-3), as a colorless oil (42 mg, 79%). $^1$H NMR (300 MHz, CDCl$_3$) δ7.02 (s, 1 H), 6.75 (dd, J=8.1, 1.2 Hz, 1 H), 6.61 (d, J=8.3 Hz, 1 H), 6.55 (s, 2 H), 5.77—5.65 (m, 1 H), 5.08 (d, J=16.9 Hz, 1 H), 4.93 (d, J=10.2 Hz, 1 H), 4.64 (s, 2 H), 4.49 (t, J=7.9 Hz, 1 H), 3.16 (heptet, J=6.9 Hz, 1 H), 3.06—2.98 (m, 1 H), 2.78—2.68 (m, 1 H), 2.14 (br. s, 6 H), 1.19 (app. t, J=7.7Hz, 6H).

HRMS exact mass calcd for C$_{23}$H$_{28}$O$_4$:368.1988, found: 368.1994.

EXAMPLE 14

Preparation of Compound (I-4), a Compound of Formula I

Preparation of Comipound (27)

To a stirred solution of Compound (26) (320 mg, 0.579 mmol, from Example 13) in anhydrous THF (5 ml) was added borane (IM in THF, 790 mmol), after 20 hr., a mixture of sodium hydroxide (0.29 mmol) and hydrogen peroxide (30%, 60μl, 0.579 mmol) was added. After 1 hr., reaction was quenched with saturated NH$_4$Cl and the aqueous phase extracted with diethyl ether. Combined organic fractions were dried (MgSO$_4$), filtered, and solvent was removed by rotary evaporation. Column chromatography (silica, 1"×7", 15%→25% EtOAc/Hexanes) yielded the alcohol, Compound (27), as a colorless oil (170 mg, 51%).

Preparation of Compound (28)

To a stirred solution of Compound (27) (67 mg, 0.12 mmol) in anhydrous THF (4 ml) was added triethylamine trihydrofluoride (1.9 ml, 12 mmol). Reaction was stirred 15 hr. then quenched with 20 ml saturated NaHCO$_3$ and extracted with diethyl ether. Combined organic fractions were dried (MgSO$_4$), filtered through Celite, and solvent was removed by rotary evaporation. Column chromatography (silica, 0.5"×5", 30% EtOAc→40% EtOAc/2% AcOH/Hexanes) yielded the phenol, Compound (28) (33 mg, 66%). $^1$H NMR (300MHz, CDCl$_3$) δ6.98 (s, 1 H), 6.74 (dd, J=8.2, 1.3 Hz, 1 H), 6.60 (d, J=8.2 Hz, 1 H), 6.54 (s, 2 H), 4.58 (s, 2 H), 4.41—4.36 (m, 1 H), 4.28 (q, J=7.1 Hz, 2 H), 3.66 (t, J=6.4 Hz, 2 H), 3.17 (heptet, J=6.9 Hz, 1 H), 2.39—2.27 (m, 1 H), 2.13—1.97 (br. m, 7 H), 1.68—1.56 (m, 1 H), 1.45—1.35 (m, 1 H), 1.29 (t, J=7.2 Hz, 3 H), 1.19 (d, J=7.1 Hz, 3 H), 1.17 (d, J=7.0 Hz, 3 H).

Preparation of Compound (I-4)

To a stirred solution of Compound (28) (33 mg, 0.080 mmol) in methanol (3 ml) was added lithium hydroxide monohydrate (7.4 mg, 0.18 mmol) and water (8111, 0.4 mmol). Reaction was stirred 13 hr., then solvent was removed by rotary evaporation. The residue was resuspended in ½-saturated NH$_4$Cl and extracted with chloroform. Combined organic fractions were dried (MgSO$_4$), filtered through Celite, and solvent was removed by rotary evaporation to yield the oxyacetic acid, Compound (I-4), as a white solid (22 mg, 71%). $^1$H NMR (300MHz, CDCl$_3$) δ 6.97 (s, 1 H), 6.73 (d, J=7.6 Hz, 1 H), 6.64 (d, J=8.2 Hz, 1 H), 6.57 (s, 2 H), 4.58 (s, 2 H), 4.43—4.38 (m, 1 H), 3.59 (t, J=6.4 Hz, 2 H), 3.23 (heptet, J=6.9 Hz, 1 H), 2.39—2.27 (m, 1 H), 2.25—1.96 (br. m, 7 H), 1.63—1.54 (m, 1 H), 1.42—1.32 (m, 1 H), 1.17 (d, J=7.2 Hz, 3 H), 1.13 (d, J=7.3 Hz, 3 H).

HRMS exact mass calcd for C$_{23}$H$_{30}$O$_5$:386.2093, found: 386.2096.

EXAMPLE 15

Preparation of Compound (I-5) a Compound of Formula I

Preparation of Compound (29)

To a stirred solution of the phenol (compound of Formula 15 from Example 11) (2.78 g, 6.08 mmol) in anhydrous DMF (10 ml), was added methyl bromoacetate (864μL, 9.13 mmol) and potassium carbonate (1.69 g, 12.2 mmol). Reaction was quenched after 6 hr. by slow addition of dilute HCl (1M, 30 ml). Mixture was diluted with 150 ml water and extracted with diethyl ether. Combined organic fractions were washed twice with brine, then dried (MgSO$_4$), filtered through a Celite plug and solvent removed by rotary evaporation to yield the methyl ether, Compound (29) as a pale yellow oil (3.7 g, 100%). $^1$H NMR (300 MHz, CDCl$_3$) δ7.15 (d, J=0.9 Hz, 1 H), 6.71 (dd, J=8.3, 1.6 Hz, 1 H), 6.63 (d, J=8.4 Hz, 1 H), 6.57 (s, 2 H), 5.70 (s, 1 H), 4.63 (s, 2 H), 3.82 (s, 3 H), 3.32 (app. s, 4 H), 2.22 (s, 6 H), 1.26 (heptet, J=7.3 Hz, 3 H), 1.15 (app. t, J=6.5Hz,6H), 1.09(d,J=7.2 Hz, 18 H).

Preparation of Compound (30)

To a stirred solution of Compound (29) (150 mg, 0.28 mmol) and 1,3-dimethyoxybenzene (470 mg, 3.4 mmol) in anhydrous methylene chloride (7 ml), chilled to −45° C., was added TFA (220μl, 2.8 mmol). After stirring 90 min, while allowing gradual warming, reaction was quenched with 13 ml saturated NaHCO$_3$, and the aqueous phase was extracted with diethyl ether. Combined organic fractions were dried (MgSO$_4$), filtered through Celite, and solvent was removed by rotary evaporation to yield Compound (30) as a colorless oil (586 mg), which was used without further purification.

Preparation of Compound (31)

To a stirred solution of Compound (30) (crude, approx. 0.26 mmol) in anhydrous THF (5 ml) was added triethylamine trihydrofluoride (4.6 ml, 28 mmol). After 10 hr., reaction was quenched with 15 ml 4M NaOH. The aqueous phase was extracted with diethyl ether and the combined organic fractions were dried (MgSO$_4$), filtered through Celite, and solvent was removed by rotary evaporation. Column chromatography (silica, 1"×6", 15%→35% EtOAc/Hexanes) yielded Compound (31) (74 mg, 55% yield from Compound (29)). $^1$H NMR (300MHz, CDCl$_3$) δ6.81 (s, 1 H), 6.74 (d, J=8.4 Hz, 1 H), 6.58 (s, 2 H), 6.54 (s, 2 H), 6.47 (d, J=2.1 Hz, 1 H), 6.36 (dd, J=8.5, 2.1 Hz, 1 H), 5.90 (s, 1 H), 4.61 (s, 2 H), 3.81 (s, 3 H), 3.79 (s, 3 H), 3.66 (s, 3 H), 3.13 (heptet, J=6.9 Hz, 1 H), 1.97 (s, 6 H), 1.13 (d, J=6.9 Hz, 6 H).

Preparation of Compound (I-5)

To a stirred solution of Compound (31) (74 mg, 0.15 mmol) in methanol was added lithium hydroxide monohydrate (14 mg, 0.34 mmol) and water (15µl, 0.85 mmol). After 7 hr., solvent was removed by rotary evaporation. The residue was resuspended in 4 ml saturated NH$_4$Cl+3 ml water+1 ml 1M HCl and extracted with chloroform. Combined organic fractions were dried (MgSO$_4$), filtered through Celite, and solvent was removed by rotary evaporation to yield an oxyacetic acid, Compound (I-5), as a white semi-solid (77 mg, 100%). $^1$H NMR (300MHz, CDCl$_3$) δ6.81 (s, 1 H), 6.74 (d, J=8.5 Hz, 1 H), 6.58 (s, 2 H), 6.56 (s, 2 H), 6.47 (d, J=2.0 Hz, 1 H), 6.36 (dd, J=8.4,2.0 Hz, 1 H), 5.90 (s, 1 H), 4.65 (s, 2 H), 3.79 (s, 3 H), 3.66 (s, 3 H), 3.13 (heptet, J=6.8 Hz, 1 H), 1.98 (s, 6 H), 1.13 (d, J=6.8 Hz, 6 H).

HRMS exact mass calcd for C$_{28}$H$_{32}$O$_6$:464.2199, found: 464.2192.

EXAMPLE 16

This example illustrates the preparation of a representative pharmaceutical formulation for oral administration containing an active compound of Formula I, e.g., ethoxy-2,6-dimethyl-4'-hydroxy -3'-(1-methylethyl)diphenylmethane-4-oxyacetic acid.

| Ingredients | Quantity per Tablet, mgs. |
| --- | --- |
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

EXAMPLE 17

This example illustrates the preparation of another representative pharmaceutical formulation for oral administration containing a compound of Formula I, e.g., ethoxy-2,6-dimethyl-4'-hydroxy -3'-(1-methylethyl)diphenylmethane-4-oxyacetic acid.

| Ingredients | Quantity per Tablet, mgs. |
| --- | --- |
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

EXAMPLE 18

This example illustrates the preparation of a representative pharmaceutical formulation containing a compound of Formula I, e.g., ethoxy-2,6-dimethyl-4'-hydroxy -3'-(1-methylethyl)diphenylmethane-4-oxyacetic acid.

An oral suspension is prepared having the following composition.

| Ingredients | Quantity |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

EXAMPLE 19

This example illustrates the preparation of a representative pharmaceutical formulation for oral administration containing an active compound of Formula I, e.g., ethoxy-2,6-dimethyl-4'-hydroxy -3'-(1-methylethyl)diphenylmethane-4-oxyacetic acid.

An injectable preparation buffered to a pH of 4 is prepared having the following composition:

| Ingredients | Quantity |
| --- | --- |
| Active Compound | 0.2 g |
| Sodium Acetate Buffer Solution (0.4M) | 2.0 ml |
| HCl (1N) | q.s. to pH 4 |
| Water (distilled, sterile) | q.s. to 20 ml |

Other compounds of Formula I can be used as the active compound in the preparation of the injectable formulations of this example.

EXAMPLE 20

This example illustrates the preparation of a representative pharmaceutical formulation for topical application containing a compound of Formula I, e.g., ethoxy-2,6-dimethyl-4'-hydroxy-3'-(1-methylethyl)diphenylmethane-4-oxyacetic acid.

| Ingredients | grams |
| --- | --- |
| Active compound | 0.2–10 |
| Span 60 | 2 |
| Tween 60 | 2 |
| Mineral oil | 5 |

-continued

| Ingredients | grams |
| --- | --- |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I can be used as the active compound in the preparation of 2P the topical formulations of this example.

EXAMPLE 21

This example illustrates the preparation of a representative pharmaceutical formulation containing a compound of Formula I, e.g., ethoxy-2,6-dimethyl-4'-hydroxy -3'-(1-methylethyl)diphenylmethane-4-oxyacetic acid.

A suppository totaling 2.5 grams is prepared having the following composition:

| Ingredients | Quantity |
| --- | --- |
| Active Compound | 500 mg |
| Witepsol H-15* | balance |

(*triglycerides of saturated vegetable fatty acid; a product of Riches-Nelson, Inc., New York, NY)

Other compounds of Formula I can be used as the active compound in the preparation of the suppository formulations of this example.

EXAMPLE 22

Receptor Binding Assays of TR Ligands

To test the ability of synthesized human thyroid receptor (hTR) ligands to bind to two subtypes of hTR, hTRα and hTRβ, the binding affinity of a TR ligand for a TR can be assayed using TRs expressed in *E. coli* and $[^{125}I]$ $T_3$ (radiolabeled 3,5,3'-triiodo-L-thyronine) using the method described by Apriletti et al., *Protein Expression and Purification*, 6:363–370 (1995), and by Apriletti et al., *J. Biol. Chem.* (1988) which are incorporated herein by reference. The TR binding experiment is conducted using the recombinant TRs in the presence of the sample to be assayed, 1 nM $[^{125}I]T_3$, and 50μg/ml core histones, in buffer E (400 mM KCl, 200 mM potassium phosphate, pH 8.0, 0.5 mM EDTA, 1 mM $MgCl_2$, 10% glycerol, 1 mM DTT) in a volume of 0.21 ml. After incubation overnight at 4° C., 0.2 ml of the incubation mixture is loaded onto a Quick-Sep Sephadex G-25 column (2.7×0.9 cm, 1.7 ml bed volume) equilibrated with buffer E. The excluded peak of protein-bound $[I^{25}]T_3$ is eluted with 1 ml of buffer E, collected in a test tube, and counted. Specific $T_3$ binding is calculated by subtracting nonspecific binding from total binding. The binding affinity of a ligand for its receptor is defined by a constant termed Kd and can be calculated using a curve fitting program.

Competition by analogues Compounds (I-1) (I-2) and (I-3) for $[^{25}I]T_3$ binding to hTRα and β

The ability of $[^{125}I]$ $T_3$ and each of Compounds (I-1), (I-2) and (I-3) to compete for binding to human recombinant TRa and separately human recombinant TRβ was measured through competition assays. In control experiments, either purified recombinant hTRα or hTRβ was incubated with $[^{125}I]$ $T_3$ and increasing concentrations ($10^{-10}$ M to $10^{-7}$ M) of unlabelled $T_3$, and the ability of $[^{125}I]$ $T_3$ to compete with unlabelled $T_3$ for binding to each of the two TR subtypes was measured. As expected, the unlabelled $T_3$ was able to compete out $[^{125}I]$ $T_3$ in binding to both hTRα or hTRβ, with Kd values of about 0.069 nM and 0.040 nM respectively. To test the analogues, either purified recombinant hTRα or hTRβ was incubated with $[^{125}I]$ $T_3$ and increasing concentrations of unlabelled Compound (I-3) ($10^{-7}$ M to $10^{-4}$ M) or Compound (I-1) ($10^{-8}$ M to $10^{-5}$ M) or Compound (I-2) ($10^{-8}$ M to $10^{-5}$ M). The ability of each analogue to compete with $T_3$ for binding to each of the two TR subtypes was measured. Unlabelled Compound (I-3) was able to compete with $[^{125}I]$ $T_3$ for binding to either hTRα or hTRβ, with Kd values of about 138nM and 36 nM respectively. Unlabelled Compound (I-1) was able to compete with $[^{125}I]$ $T_3$ for binding to either hTRα or hTRβ, with Kd values of about 77nM and 180nM respectively. Unlabelled Compound (I-2) was able to compete with $[^{125}I]$ $T_3$ for binding to either hTRα or hTRβ, with Kd values of about 237nM and 721nM respectively.

EXAMPLE 23

Cellular Transcription Assay of TR Ligands

Cell Culture, Transfections and Luciferase Assay

Cellular transactivation assays can be performed according to the procedure in Ribeiro R. C. et al. (1996) *J. Biol. Chem.* 271, 17147–17151. Briefly, HeLa cells are grown in 15 cm dishes in DME H-21, 4.5 g/L glucose with 10% newborn bovine serum, 2 mM glutamine, 50 units/ml penicillin, and 50 μg/ml streptomycin.

For transfections, cells are trypsinized, resuspended in buffer (PBS, 0.1% glucose), and mixed with a reporter gene construct and with or without the appropriate thyroid receptor (TR) expression vectors (CMV TR $β_1$, CMV TR $α_1$). One such reporter gene construct consists of a synthetic TR response element (DR-4) containing two copies of a direct repeat spaced by four nucleotides (AGGTCA-caggAGGTCA) cloned into the HindIII site of the pUC19 polylinker immediately upstream of a minimal (−32/+45) thymidine kinase promoter linked to luciferase coding sequences. Another reporter gene construct that can be used consists of the β-galactosidase coding sequence fused downstream of an actin promoter.

Cells in 0.5 ml of buffer (8+/−2 million cells) are electroporated using a Bio-Rad gene pulser at 0.35 kvolts and 960 microfarads. After electroporation, cells are pooled in growth medium (DME H-21 with 10% charcoal-treated, hormone stripped, newborn bovine serum), plated in 6-well dishes, and are treated with either vehicle (ethanol), hormone ($T_3$), or analogue (the test ligand). T3 and the test ligand are used at a range of selected concentrations. After incubation at 37° C. for 24 hours, incubation media is discarded and the cells are detached with 1 ml of calcium/magnesium-free PBS, 1mM EDTA, prewarmed at 37° C., and transferred to 1.5 ml Eppendorf tubes. Cells are pelleted by centrifugation in a microfuge for 15 seconds at room temperature. The supernatants are aspirated and the pellets are lysed by addition of 120 μl of Tris-Cl 0.25 M pH 7.6, 0.1% Triton. After resuspension by vortexing for 5–10 sec, the lysates are pelleted by centrifugation in a microfuge for 5 min at room temperature. One hundred µl of each Eppendorf tube lysate is added to 300 µl of 25 mM glycylglycine pH 7.8, 15 mM MgSO$_4$, 4 mM EGTA, 15 mM potassium phosphate pH 7.8, 1 mM DTT, 2 mM ATP, and 0.2 mM Luciferine. The light output is measured for 10 sec at room temperature with a luminometer (Analytical Luminescence Laboratory, MONOLIGHT$^R$1500).

Transcription Activation of TR by Comnpounds (I-1) and (I-3)

The ability of Compound (I-1) and Compound (I-3) to activate transcription via each of the two subtypes of hTR was measured by Luciferase assay. In control experiments, HeLa cells overexpressing either hTRα or hTRβ and containing the luciferase reporter gene construct were incubated with increasing concentrations ($10^{-12}$ to $10^{-7}$ M) of T$_3$. The ability of T$_3$ to bind to each of the two hTR subtypes, interact with the TR response element on the reporter gene construct and allow the downstream promoter to drive the expression of the luciferase protein was measured. Luciferase elicits a light output than allows for detection of the expressed protein. As expected, T$_3$ was able to activate transcription and translation of the luciferase gene. To test analogue Compounds (I-3) and (I-1), HeLa cells overexpressing either hTRα or hTRβ and containing the luciferase reporter gene construct were incubated with increasing concentrations of Compound (I-3) ($10^{-10}$ M to $3 \times 10^{-5}$ M) or Compound (I-1) ($10^{-9}$ M to $3 \times 10^{-5}$ M). Compound (I-3) was able to stimulate transcription and translation of the luciferase gene through both subtypes of hTR, though to a lesser degree than. T$_3$, indicating that Compound (I-3) may serve as a weak agonist of both hTRα and hTRβ. Compound (I-1) did not appear to activate hTR-mediated transcription though was still able to compete with T3, indicating that Compound (I-1) may serve as an antagonist of both hTRα and hTRβ.

To further test analogue Compound (I-l)'s role, HeLa cells containing the luciferase reporter gene construct and the β-galactosidase reporter gene construct, but no overexpressed hTRs were incubated with increasing concentrations of Compound (I-1) ($10^{-6}$ M to $3 \times 10^{-5}$ M) and/or 1nM T3. This experiment showed that the luciferase activity seen at the highest concentration [$10^{-5}$] of Compound (I-1) occurs even when a TR-expression construct is not cotransfected into HeLa cells, and subsequently correlates with toxicity as defined by, for example, a change in cell morphology, or lifting off of cells from a growth surface, observed in the micromolar range (10µM). These results indicate that the observed luciferase activity is not due to the overexpression of thyroid hormone receptors in HeLa cells. In addition, expression of β-galactosidase was not affected by the presence of 1nM T3 or increasing concentrations of Compound (I-1) ($10^{-6}$ M to $10^{-5}$ M), indicating that the decrease in reporter gene activity observed in the competition experiment between T3 and Compound (I-1) was not likely to be due to a decrease in cell density.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound Formula I:

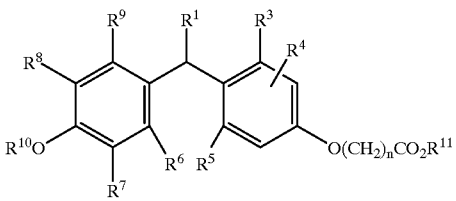

wherein:

n is 1, 2 or 3;

R$^1$ is C$_{3-12}$alkanol, C$_{2-6}$alkenyl, C$_{5-12}$alkenol, heterocyclo, aryl substituted with at least one electron-donating group, —O$^2$ or —SR$^2$, where R$^2$ is C$_{1-12}$alkyl or aryl, or —A—C(O)NR$^{12}$R$^{13}$, where A is C$_{2-15}$alkyl or C$_{4-15}$alkenyl and R$^{12}$ and R$^{13}$ are C$_{1-6}$alkyl;

R$^3$ and R$^5$ are methyl;

R$^4$ is hydrogen, C$_{1-6}$alkyl or cycloalkyl;

R$^6$ and R$^9$ are hydrogen or C$_{1-6}$alkyl;

R$^7$ and R$^8$ are independently hydrogen, halogen, C$_{1-6}$alkyl, optionally substituted phenyl, optionally substituted benzyl, or heteroaryl; with the proviso that R$^7$ and R$^8$ cannot both be hydrogen;

R$^{10}$ is hydrogen, C$_{1-6}$alkyl, cycloalkyl, or acyl; and

R$^{11}$ is hydrogen, C$_{1-6}$alkyl, or cycloalkyl; and the pharmaceutically acceptable salts thereof.

2. The compound of claim 1 wherein n is 1.

3. The compound of claim 1 wherein R$^1$ is C$_{3-12}$alkanol, C$_{2-6}$alkenyl, aryl substituted with at least one electron-donating group, —OR$^2$ or —SR$^2$, where R$^2$ is C$_{1-12}$alkyl or aryl, or —A—C(O)NR$^{12}$R$^{13}$, where A is C$_{2-15}$alkyl or C$_{4-15}$alkenyl and R$^{12}$ and R$^{13}$ are C$_{1-6}$alkyl.

4. The compound of claim 1 wherein R$^4$ is hydrogen.

5. The compound of claim 1 wherein R$^6$ is hydrogen.

6. The compound of claim 1 wherein R$^7$ is hydrogen.

7. The compound of claim 1 wherein R$^8$ is C$_{1-6}$alkyl.

8. The compound of claim 1 wherein R$^9$ is hydrogen.

9. The compound of claim 1 wherein R$^{10}$ is hydrogen.

10. The compound of claim 1 wherein R$^{11}$ is hydrogen.

11. The compound of claim 1 wherein R$^1$ is —OR$^2$.

12. The compound of claim 11 wherein n is 1; R$^1$ is ethoxy; R$^4$, R$^6$ and R$^7$ are hydrogen; R$^8$ is isopropyl; and R$^9$, R$^{10}$ and R$^{11}$ are hydrogen.

13. The compound of claim 1 wherein R$^1$ is —SR$^2$.

14. The compound of claim 13 wherein n is 1; R$^1$ is ethylthio; R$^4$, R$^6$ and R$^7$ are hydrogen; R$^8$ is isopropyl; and R$^9$, R$^{10}$ and R$^{11}$ are hydrogen.

15. The compound of claim 13 wherein n is 1; R$^1$ is phenylthio; R$^4$, R$^6$ and R$^7$ are hydrogen; R$^8$ is isopropyl; and R$^9$, R$^{10}$ and R$^{11}$ are hydrogen.

16. The compound of claim 1 wherein R$^1$ is C$_{2-6}$alkenyl.

17. The compound of claim 16 wherein n is 1; R$^1$ is —CH$_2$—CH=CH$_2$; R$^4$, R$^6$ and R$^7$ are hydrogen; R$^8$ is isopropyl; and R$^9$, R$^{10}$ and R$^{11}$ are hydrogen.

18. The compound of claim 1 wherein R$^1$ is aryl substituted with at least one electron-donating group.

19. The compound of claim 18 wherein n is 1; R$^1$ is dimethoxyphenyl; R$^4$, R$^6$ and R$^7$ are hydrogen; R$^8$ is isopropyl; and R$^9$, R$^{10}$ and R$^{11}$ are hydrogen.

20. The compound of claim 1 wherein R$^1$ is C$_{3-12}$alkanol.

21. The compound of claim 20 wherein n is 1; R$^1$ is —(CH$_2$)$_3$—OH; R$^4$, R$^6$ and R$^7$ are hydrogen; R$^8$ is isopropyl; and R$^9$, R$^{10}$ and R$^{11}$ are hydrogen.

22. The compound of claim 1 wherein $R^1$ is —A—C(O)$NR^{12}R^{13}$ and A is $C_{2-15}$alkyl.

23. The compound of claim 22 wherein n is 1; $R^1$ is —$(CH_2)_{10}$—C(O)—N(CH$_3$)—(CH$_2$)$_3$(CH$_3$); $R^4$,$R^6$ and $R^7$ are hydrogen; $R^8$ is isopropyl; and $R^9$,$R^{10}$ and $R^{11}$ are hydrogen.

24. The compound of claim 1 wherein $R^1$ is —A—C(O)$NR^{12}R^{13}$ and A is $C_{4-15}$alkenyl.

25. The compound of claim 24 wherein n is 1; $R^1$ is —$(CH_2)_2$—C=C—$(CH_2)_6$—C(O)—N(CH$_3$)—(CH$_2$)$_3$(CH$_3$); $R^4$,$R^6$ and $R^7$ are hydrogen; $R^8$ is isopropyl; and $R^9$,$R^{10}$ and $R^{11}$ are hydrogen.

26. A pharmaceutical composition for administration to a mammal having a disease state which is alleviated by treatment with a thyroid hormone antagonist, which comprises a therapeutically effective amount of a compound of claim 1 in admixture with one or more pharmaceutically acceptable excipients.

27. A method of treating a mammal having a disease state which is alleviated by treatment with a thyroid hormone antagonist, which method comprises administering a therapeutically effective amount of a compound of claim 1 to a mammal in need thereof.

28. The method of claim 27 wherein the disease state is hyperthyroidism or cardiac arrhythmia.

29. A compound of Formula II:

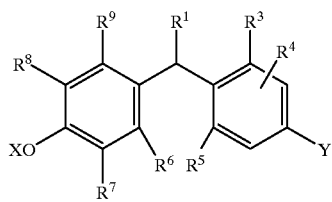

where:
Y is —OT or —O(CH$_2$)$_n$CO$_2$C$_{1-6}$alkyl;
n is 1,2 or 3;
X and T are protecting groups;
$R^1$ is $C_{3-12}$alkanol, $C_{2-6}$alkenyl, $C_{5-12}$alkenol, heterocyclo, aryl substituted with at least one electron-donating group, —OR or —SR$^2$, where $R^2$ is $C_{1-12}$alkyl or aryl, or —A—C(O)NR$^{12}$R$^{13}$, where A is $C_{2-15}$alkyl or $C_{4-15}$alkenyl and $R^{12}$ and $R^{13}$ are $C_{1-6}$alkyl;
$R^3$ and $R^5$ are methyl;
$R^4$ is hydrogen, $C_{1-6}$alkyl or cycloalkyl;
$R^6$ and $R^9$ are hydrogen or $C_{1-6}$alkyl; and $R^7$ and $R^8$ are independently hydrogen, halogen, $C_{1-6}$alkyl, optionally substituted phenyl, optionally substituted benzyl, or heteroaryl; with the proviso that $R^7$ and $R^8$ cannot both be hydrogen.

30. The compound of claim 29 wherein X is a silyl containing protecting group.

31. The compound of claim 30 wherein X is triisopropylsilyl.

32. The compound of claim 29 wherein Y is —O(CH$_2$)$_n$CO$_2$Me, —O(CH$_2$)$_n$CO$_2$Et, or —OT where T is $C_{1-6}$alkyl.

33. A compound of the formula:

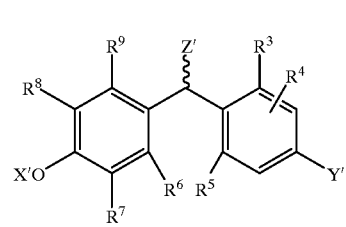

where:
Y' is —OT' or —O(CH$_2$)$_n$CO$_2$C$_{1-6}$alkyl;
n is 1, 2 or 3;
X' and T' are protecting groups, and at least one of said protecting groups is a silyl containing protecting group;
Z' is a leaving group;
$R^3$ and $R^5$ are methyl;
$R^4$ is hydrogen, $C_{1-6}$alkyl or cycloalkyl;
$R^6$ and $R^9$ are hydrogen or $C_{1-6}$alkyl; and
$R^7$ and $R^8$ are independently hydrogen, halogen, $C_{1-6}$alkyl, optionally substituted phenyl, optionally substituted benzyl, or heteroaryl; with the proviso that $R^7$ and $R^8$ cannot both be hydrogen.

34. The compound of claim 33 wherein X' is a silyl containing protecting group.

35. The compound of claim 34 wherein X is triisopropylsilyl.

36. The compound of claim 33 wherein Y' is —OT' and T' is a silyl containing protecting group.

37. The compound of claim 36 wherein T is tert-butylmethoxyphenylsilyloxy.

38. The compound of claim 33 wherein Y' is —O(CH$_2$)$_n$CO$_2$Me or —O(CH$_2$)$_n$CO$_2$Et.

39. The compound of claim 33 wherein Z' is hydroxy or lower alkoxy.

* * * * *